United States Patent [19]
Gould-Fogerite et al.

[11] Patent Number: 5,643,574
[45] Date of Patent: Jul. 1, 1997

[54] PROTEIN- OR PEPTIDE-COCHLEATE VACCINES AND METHODS OF IMMUNIZING USING THE SAME

[75] Inventors: Susan Gould-Fogerite; Raphael James Mannino, both of Annandale, N.J.

[73] Assignees: Albany Medical College, Albany, N.Y.; University of Medicine & Dentistry of New Jersey, Newark, N.J.

[21] Appl. No.: 130,986

[22] Filed: Oct. 4, 1993

[51] Int. Cl.$^6$ .......................... A61K 39/00; A61K 51/00; A61K 38/16; B01J 13/02
[52] U.S. Cl. .......................... 424/184.1; 424/121; 264/46; 514/8
[58] Field of Search .................. 424/88, 89, 92, 424/184.1, 1.21; 264/4.6; 514/8

[56] References Cited

U.S. PATENT DOCUMENTS

| | | |
|---|---|---|
| 4,078,052 | 3/1978 | Papahadjopoulos .................. 424/36 |
| 4,663,161 | 5/1987 | Mannino et al. . |
| 4,871,488 | 10/1989 | Mannino et al. . |

OTHER PUBLICATIONS

Miller et al, Vaccination of Rhesus Monkeys with Synthetic Peptide in a Fusogenic Proteoliposome Elicits Simian Immunodeficiency Virus–Specific CD8+ Cytotoxic T Lymphocytes, *J. Exp. Med.*, vol. 176, pp. 1739–1744, 1992.

R. J. Mannino and S. Gould-Fogerite, Liposome Mediated Gene Transfer, *BioTechniques*, vol. 6, No. 7, pp. 682–690, 1988.

Gould-Fogerite et al, Chimerasome-mediated gene transfer in vitro and in vivo, *Gene*, vol. 84, pp. 429–438, 1989.

S. Gould-Fogerite and R.J. Mannino, Rotary Dialysis: Its Application to the Preparation of Large-Liposomes and Large Proteoliposomes (Protein-Lipid Vesicles) with High Encapsulation Efficiency and Efficient Reconstitution of Membrane Proteins, *Analytical Biochemistry*, vol. 148, pp. 15–25, 1985.

Gould-Fogerite et al, The Reconstitution of Biologically Active Glycoproteins into Large Liposomes: Use as a Delivery Vehicle to Animal Cells, *Advances in Membrane Biochemistry and Bioenergetics*, pp. 569–586, 1988.

S. Gould-Fogerite and R.J. Mannino, Liposome Preparation and Related Techniques, *Liposome Technology 2nd Edition*, vol. I, pp. 67–80.

S. Gould-Fogerite and R.J. Mannino, Entrapment of Drugs and Other Materials, *Liposome Technology 2nd Edition*, vol. II, pp. 167–184.

S. Gould-Fogerite and R.J. Mannino, Interactions of Liposomes with the Biological Milieu, *Liposome Technology 2nd Edition*, vol. III, pp. 261–276.

G. Goodman-Snitkoff et al, Defining Minimal Requirements for Antibody Production to Peptide Antigens, *Vaccine*, vol. 8, pp. 257–262, 1990.

G. Goodman-Snitkoff et al, Role of Intrastructural/Intermolecular Help in Immunization with Peptide-Phospholipid Complexes, *The Journal of Immunology*, vol. 147, No. 2, pp. 410–415, 1991.

D. Papahadjopoulos et al, *Biochem. Biophys. Acta*, vol. 394, p. 483, 1975.

Liposome Technology, Second Edition, vol. 1, G. Gregoriadis, Ph.D., "Liposome Preparation and Related Techniques", published 1993 by CRC Press, Inc., (Boca Raton), pp. 67–80.

J. Exp. Med., vol. 176, issued Dec. 1992, M.D. Miller et al, "Vaccination of Rhesus Monkeys with Synthetic Peptide in a Fusogenic Proteoliposome Elicits Simian Immunodeficiency Virus-specific CD8+ Cytotoxic T Lymphocytes", pp. 1739–1744.

Nature, vol. 342, issued 30 Nov. 1989, K. Deres et al, "In vivo Priming of Virus-specific Cytotoxic T lymphocytes with Synthetic Lipopeptide Vaccine", pp. 561–564.

*Biochimica et Biophysica Acta*, vol. 394, issued 1975, D. Papahadjopoulos et al, "Cocheleate Lipid Cylinders: Formation By Fusion of Unilamellar Lipid Vesciles", pp. 483–491.

C. H. Kim et al, "Advances in Membrane Biochemistry and Bioenergetics" published 1988 by Plenum Publishing Corporation, pp. 569–586.

*Primary Examiner*—James C. Housel
*Assistant Examiner*—N. M. Minnifield
*Attorney, Agent, or Firm*—Sughrue, Mion, Zinn, Macpeak & Seas

[57] ABSTRACT

A method is described of immunizing a host by administering a biologically effective amount of a protein- or peptide-cochleate comprising at least a protein or peptide to which an immune response is elicited, a negatively charged lipid, and a divalent cation.

26 Claims, 25 Drawing Sheets

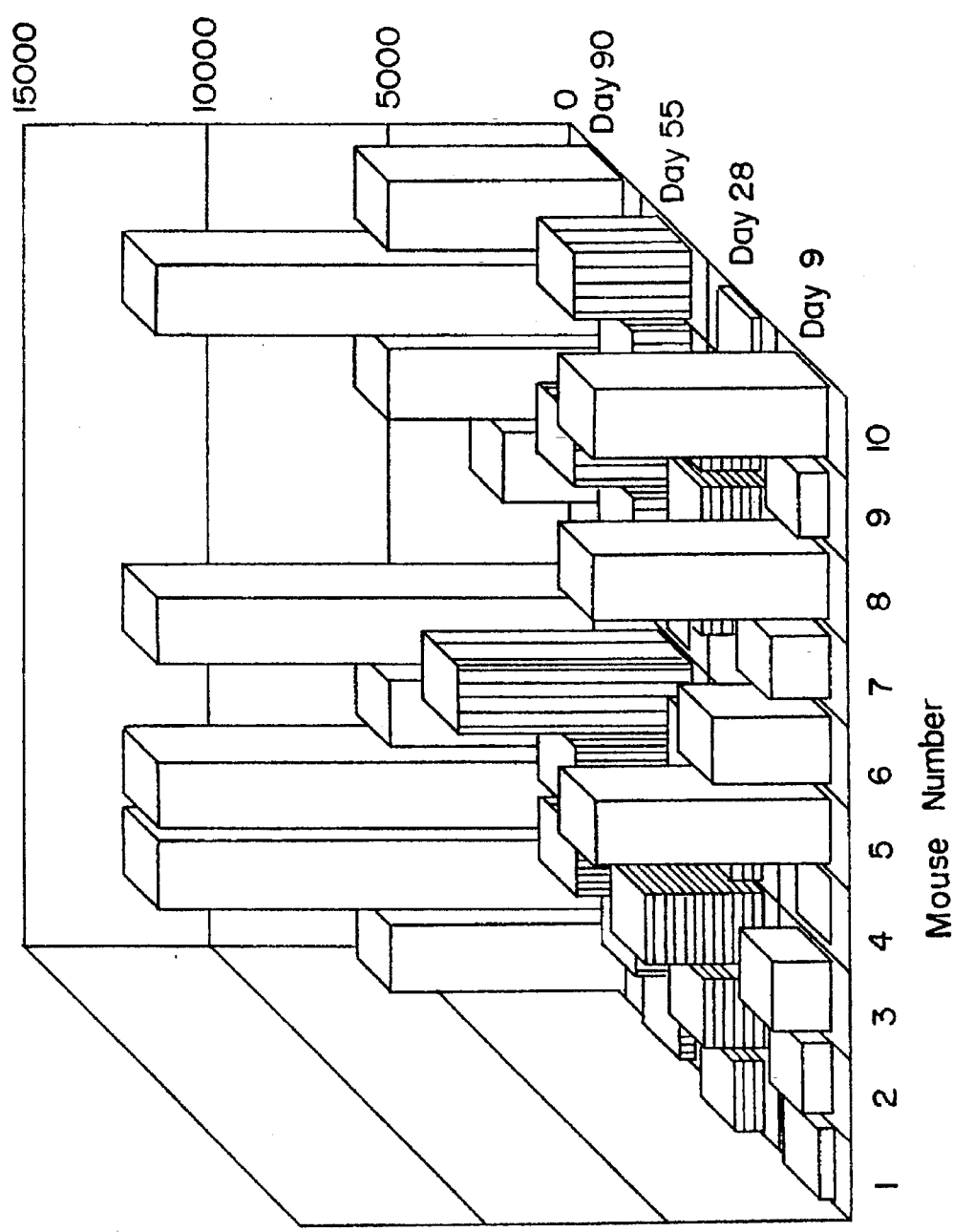

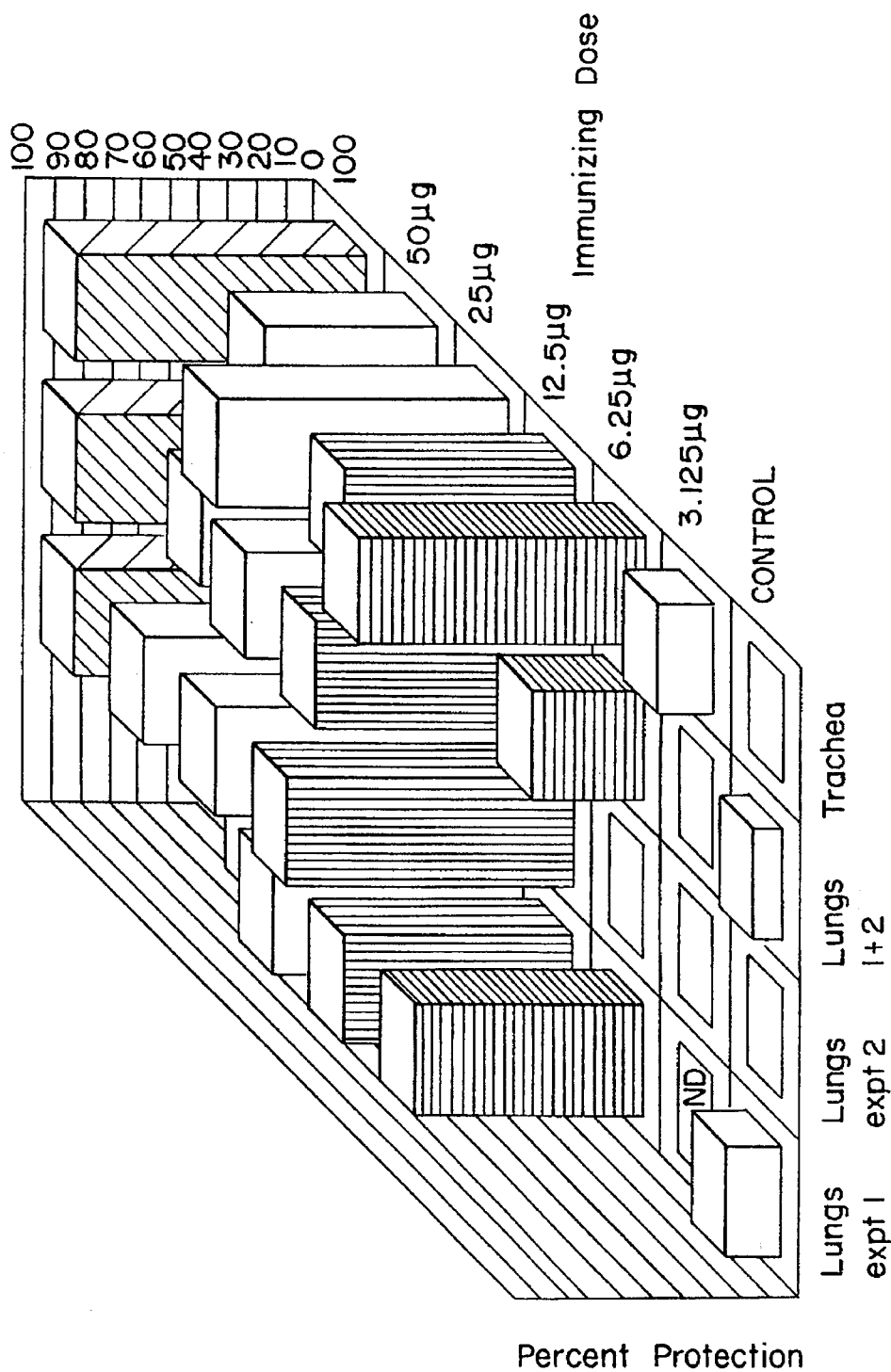

PROTEIN- OR PEPTIDE-COCHLEATE VACCINES AND METHODS OF IMMUNIZING USING THE SAME

Portions of the subject matter disclosed herein were supported in part by monies or grants from the United States Government.

FIELD OF THE INVENTION

The present invention relates to protein- or peptide-cochleate vaccines and methods of immunizing using protein- or peptide-cochleate structures. These unique vaccines are composed of insoluble antigen-lipid-divalent cation structures which can be administered orally as well as by conventional routes and which generate mucosal as well as circulating immune responses. Protective immunity against live pathogen challenge on a mucosal surface is demonstrated.

BACKGROUND OF THE INVENTION

Plain lipid cochleates (FIG. 1) have been described previously. Protein- or peptide-cochleates have been described heretofore and patented by the present inventors, as intermediate structures which can be converted to protein-lipid vesicles (proteoliposomes) (FIG. 2) by the addition of calcium chelating agents (see U.S. Pat. No. 4,663,161 and U.S. Pat. No. 4,871,488, the disclosures of which are expressly incorporated herein by reference). The structure of a protein- or peptide-cochleate is thought to be similar, perhaps with protrusions or bulges around the protein or peptide moieties. Indeed, a freeze-fracture electron micrograph of cochleates containing Sendai glycoproteins made by the DC method shows the rolled up lipid bilayer structures with a "bumpy" surface (FIG. 3). Plain phospholipid cochleates are smooth in this type of preparation. These proteoliposomes resulting from protein- or peptide-cochleates have been shown to be effective immunogens when administered to animals by intraperitoneal and intramuscular routes of immunization (G. Goodman-Snitkoff, et al., *J. Immunol.*, Vol. 147, p.410 (1991); M. D. Miller, et al., *J. Exp. Med.*, Vol. 176, p. 1739 (1992)). Further, when the glycoproteins of Sendai or influenza viruses are reconstituted by this method, these proteoliposomes are effective delivery vehicles for proteins and DNA to animals and to cells in culture (R. J. Mannino and S. Gould-Fogerite, *Biotechniques*, Vol. 6, No. 1, pp. 682–690 (1988); S. Gould-Fogerite et al., *Gene*, Vol. 84, p. 429 (1989); M. D. Miller, et al., *J. Exp. Med.*, Vol. 176, p. 1739 (1992)). Nonetheless, it would be advantageous to provide additional configurations for synthetic vaccines. It would also be advantageous to provide synthetic vaccines in a form that is stable at room temperature and that is suitable for oral administration. As a result of investigations in this area, the present invention was made.

SUMMARY OF THE INVENTION

Accordingly, it is an object of this invention to provide vaccines and a method of immunizing, wherein the vaccine is composed of an insoluble antigen-lipid-divalent cation structure which, following administration, including oral, i.e., peroral, administration, can induce mucosal and circulating, humoral and cell mediated immune responses.

These and other objects have been obtained by providing a vaccine comprising an immunologically effective amount of a protein- or peptide-cochleate, wherein said protein- or peptide-cochleate comprises the following components:

a) a protein or peptide component to which an immune response can be elicited, b) a negatively charged lipid component, and c) a divalent cation component.

The present invention also provides a method of immunizing comprising administering to a host a biologically effective amount of the above-described protein- or peptide-cochleate.

In a preferred embodiment, the vaccine is administered orally.

The advantages of immunizing with cochleates are numerous. The cochleates have a non-aqueous structure and therefore they:

(a) are more stable because of less oxidation of lipids;

(b) can be stored lyophilized which provides the potential to be stored for long periods of time at room temperatures, which would be advantageous for worldwide shipping and storage prior to administration;

(c) maintain their structure even after lyophilization, whereas liposome structures are destroyed by lyophilization;

(d) exhibit efficient incorporation of antigens with hydrophobic moieties into the lipid bilayer of the cochleate structure;

(e) have the potential for slow release of antigen in vivo as cochleates slowly unwind or otherwise dissociate;

(f) have a lipid bilayer matrix which serves as a carrier and is composed of simple lipids which are found in animal and plant cell membranes, so that the lipids are non-toxic, non-immunogenic and non-inflammatory;

(g) contain high concentration of calcium, an essential mineral;

(h) are safer than live vaccines, since the cochleates are non-living subunit formulations, and as a result the cochleates have none of the risks associated with use of live vaccines, such as life threatening infections in immunocompromised individuals or reversion to wild type infectivity which poses a danger to even healthy people;

(i) are produced easily and safely; and (j) can be produced as defined formulations composed of predetermined amounts and ratios of antigens, including proteins, peptides, carbohydrates, and nucleic acids.

The advantages of oral vaccination are also numerous. An oral route has been chosen by the WHO Children's Vaccine Initiative because of ease of administration and opportunity to prime the mucosal immune system. Oral vaccines are less expensive and much safer to administer than parenterally (intramuscular or subcutaneous) administered vaccines. The use of needles adds to the cost, and also, unfortunately, in the field, needles are often reused. This can lead to spread of disease between vaccinated individuals and could be potentially disastrous in areas where there is a high incidence of infection with human immunodeficiency virus (HIV) which causes AIDS. Further, oral, nasal, ocular and vaginal mucous membranes are the primary routes of entry for a large number and wide variety of human disease-causing agents. Intramuscular or subcutaneous administration of vaccines often does not lead to significant protection against these infectious agents. In contrast, the oral route of delivery can stimulate strong protective responses on mucous membranes and in the circulation.

BRIEF DESCRIPTION OF THE DRAWINGS

FIG. 6 is a graph showing serum antibody titers following a single oral dose of influenza protein-cochleates.

FIG. 7 is a graph showing the results of oral administration of protein- or peptide-cochleares when challenged with live virus. In the figure, "ND" means "not determined".

DETAILED DESCRIPTION OF THE INVENTION

Figure 1:
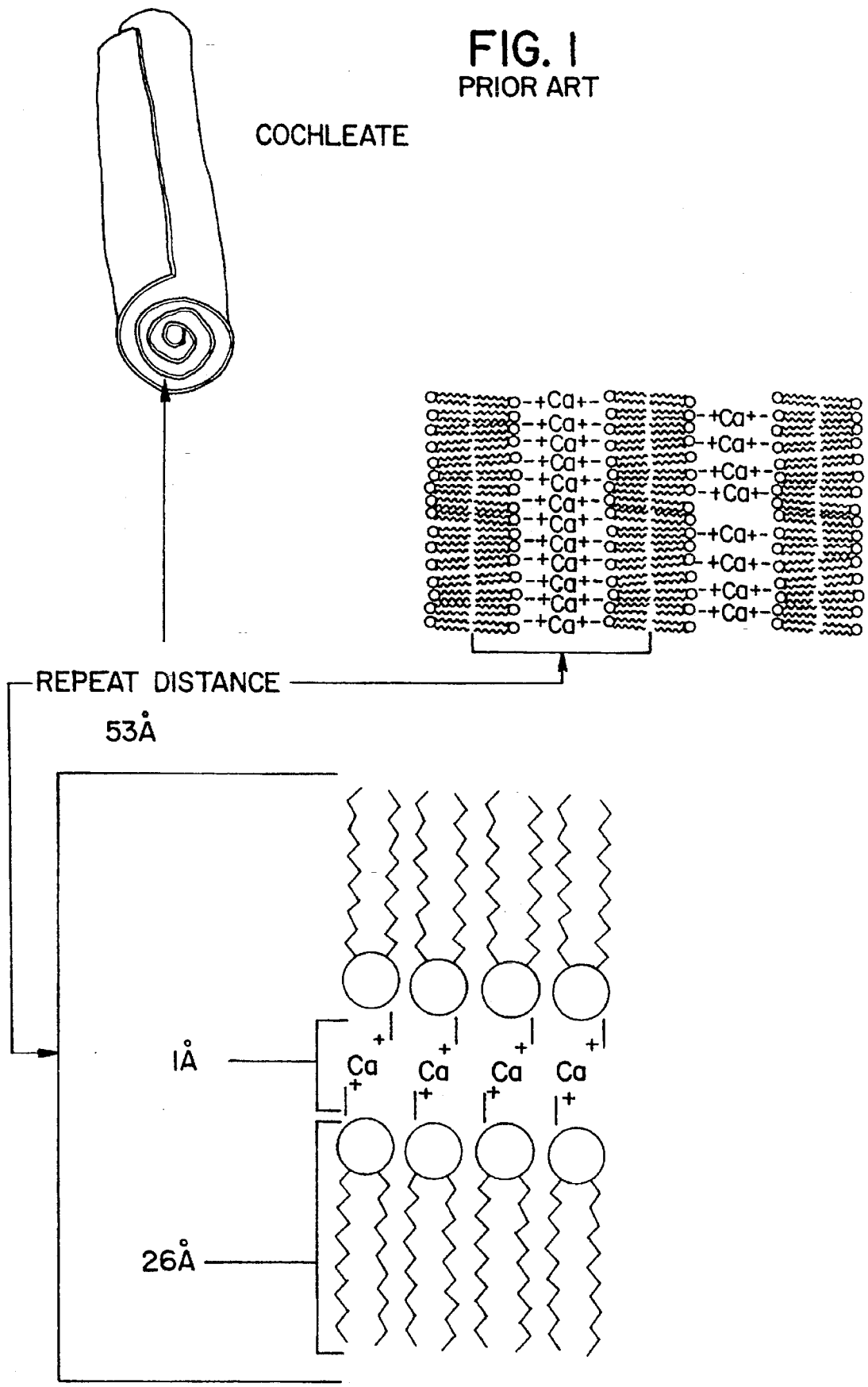
FIG. 1 is a schematic representation of a plain lipid cochleate.
Figure 2:
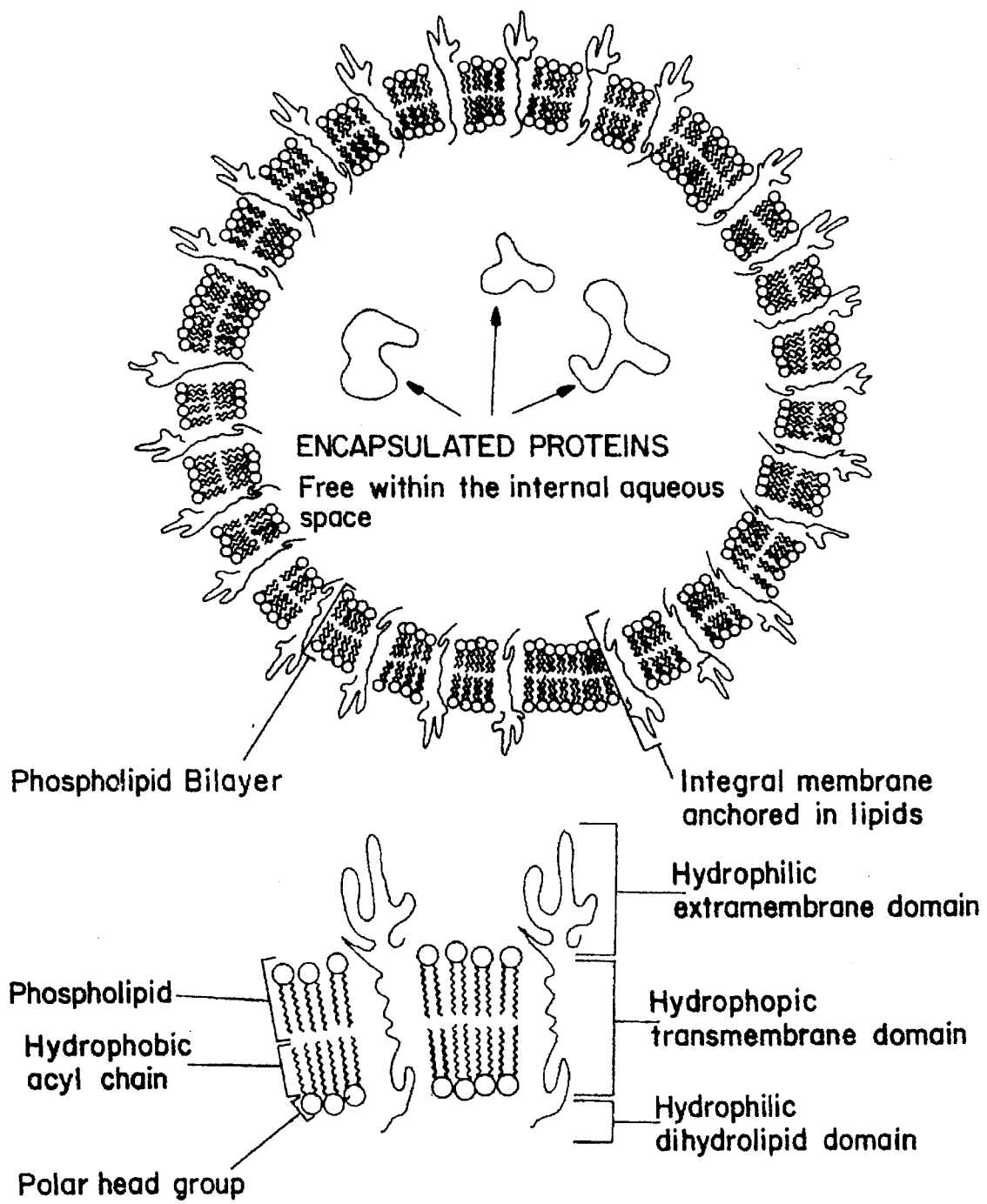
FIG. 2 shows the structure of protein-lipid vesicles with integrated membrane proteins.
Figure 3:
FIG. 3 is a freeze-fracture electron micrograph of a protein- or peptide-cochleate. The inset bar is 0.1 micrometers.

The present inventors have now found surprisingly and have demonstrated that protein- or peptide-cochleate structures can themselves be used as vaccines, including oral vaccines. These cochleates apparently survive the harsh acid environment of the stomach, protecting the delicate proteins within them, probably by virtue of their unique multilayered precipitate structure. It is likely that they are then taken up by microfold cells (M cells) in the small intestine, where they are presented to T and B cells. Appropriate stimulation of these cells by foreign proteins can lead to blood borne (circulatory) and mucous membrane borne (mucosal) immune responses. These can be humoral (antibody) and cell mediated (helper or cytotoxic "killer" cell) responses.

The present inventors have demonstrated that oral administration by drinking cochleates containing the glycoproteins and viral lipids from the surface of influenza or Sendai viruses plus phosphatidyl serine and cholesterol, stimulate both mucosal and circulating antibody responses. In addition, strong helper cell (proliferative) and killer (cytotoxic) cell responses are also generated. Perhaps most impressively, oral administration of the influenza cochleates has been shown to protect against intranasal challenge with live virus.

These results are unexpected for a number of reasons.

It was not known and was not expected that the cochleate structures would survive the stomach and protect the proteins associated with them from its acid environment and degradative enzymes. It is known that without the presence of at least 3 mM calcium, the cochleates begin to unwind and form liposomes. It was possible, in fact likely, that the cochleates would not remain intact during the transit from the mouth, down the esophagus, and through the stomach. If they did come apart, they would be digested as food.

Despite the attractiveness of the oral route for vaccine administration because of its ease and the possibility of priming the mucosal immune system, very little success has been achieved in this area. Positive results have mainly been limited to viruses and bacteria which have evolved to infect using the oral route of entry to eventually replicate in the gut, (e.g., polio virus). Enveloped viruses such as influenza and Sendai (and liposomes made from them) do not have the appropriate physical characteristics to efficiently survive the stomach and small intestinal degradation environments. Additionally, it has been difficult to achieve significant circulatory immune responses using nonliving vaccines administered only by the oral route. Some success has been achieved using multiple intramuscular priming boosts and then following with oral boosting. To the inventors' knowledge, the present invention is the only system where oral administration of a subunit vaccine which is not or does not contain parts of an organism which infects the gastrointestinal tract has led to significant circulating and mucosal antibody responses, and cell mediated immunity. The fact that the mucosal (and circulating) responses were significant enough to protect mice from viral replication in the trachea and lungs following intranasal challenge, makes these results all the more novel and significant.

Also, having survived the stomach, that these structures would interact in an effective way with the mucosal and circulating immune systems was unknown and unexpected. Everyone ingests large quantities of proteins, fats and sugars on a daily basis which simply get digested and used as fuel, without stimulating any kind of mucosal or circulating immune responses. Yet, the body needs to be able to respond to infectious organisms which enter and infect by this route. The parameters which regulate the outcome of introduction of proteins via this route, i.e., immune response, lack of response, or tolerance, are not currently understood. Given the difficulty in using the oral route to get good immune responses to non-live vaccines, and the lack of understanding of the regulatory mechanisms involved, the ability to use cochleate structures to induce strong circulating and mucosal immune responses could not be predicted.

As used herein, the term "immune response" means either antibody, cellular, proliferative, or cytotoxic activities, or secretion of cytokines.

The protein- or peptide-cochleates used in the vaccine and method according to the present invention can be prepared by known methods such as those described in U.S. Pat. No. 4,663,161, filed Apr. 22, 1985, U.S. Pat. No. 4,871,488, filed Apr. 13, 1987, S. Gould-Fogerite et al., *Analytical Biochemistry*, Vol. 148, pages 15–25 (1985); S. Gould-Fogerite et al., *Advances in Membrane Biochemistry and Bioenergetics*, edited by Kim, C. H., Tedeschi, T., Diwan, J. J., and Salerno, J. C., Plenum Press, New York, pages 569–586 (1988); S. Gould-Fogerite et al., *Gene*, Vol. 84, pages 429–438 (1989); *Liposome Technology*, 2nd Edition, Vol. I, Liposome Preparation and Related Techniques, Vol. II, Entrapment of Drugs and Other Materials, and Vol. III, Interactions of Liposomes with the Biological Milieu, all edited by Gregory Gregoriadis (CRC Press, Boca Raton, Ann Arbor, London, Tokyo), Chapter 4, pp 69–80, Chapter 10, pp 167–184, and Chapter 17, pp. 261–276 (1993); and R. J. Mannino and S. Gould-Fogerite, Liposome Mediated Gene Transfer, *Biotechniques*, Vol. 6, No. 1 (1988), pp. 682–690. In the initial step of these methods, a desired immunogen which can be a peptide or protein, a carbohydrate, or DNA, is prepared.

The immunogen is extracted out from the source particle, cell, tissue, or organism by known methods. Preferably the immunogen is a peptide or protein. Preferably the peptide or protein is a glycoprotein or membrane protein, and more preferably a membrane glycoprotein. Biological activity of proteins need not be maintained. However, in some instances (e.g., where a protein has membrane fusion or ligand binding activity or a complex conformation which is recognized by the immune system), it is desirable to maintain the biological activity of a protein. In these instances, an extraction buffer containing a detergent which does not destroy the biological activity of the membrane protein is used. Suitable detergents include ionic detergents such as cholate salts, deoxycholate salts and the like or nonionic detergents such as those containing polyoxyethylene or sugar head groups or heterogeneous polyoxyethylene detergents such as TWEEN or BRIG or TRITON. Preferred detergents are nonionic detergents containing sugar head groups such as the alkyl glucosides. A particularly preferred nonionic detergent for this purpose is β-D-octyl-glucopyranoside.

Utilization of this method allows efficient association with the cochleates and, eventually, reconstitution of the membrane proteins into the liposomes with retention of biological activities. This step avoids previously utilized organic solvents, sonication, or extremes of pH, temperature, or pressure, all of which may have an adverse effect upon efficient reconstitution in a biologically active form of the desired membrane proteins.

The buffer component utilized in conjunction with the aforesaid detergents can be any conventional buffer employed for membrane protein extractions. A suitable extraction buffer for the present purposes can be prepared utilizing a 2M NaCl, 0.02M sodium phosphate buffer (pH 7.4). The concentration of the detergent component in the buffer is not narrowly critical and can be in the range of from 0.1 to 20% (w/v) preferably from 1 to 5%, most preferably about 2%. The extraction efficiency can be enhanced by utilizing techniques well known in the art, such as by vortexing and sonicating.

The extracted membrane proteins are removed from non-soluble debris by procedures well known in the art, such as for example by centrifugation or chromatography. The resulting supernatant containing the extracted membrane protein may then be applied directly in the cochleate formation procedure.

Membrane proteins which can be employed in the practice of the present invention include viral proteins such as for example viral envelope protein, animal cell membrane protein, plant cell membrane protein, bacterial membrane protein, parasite membrane protein, viral membrane protein and the like. These respective proteins can be separated from other components by procedures well known in the art prior to introduction into the present methodology or they can be resolved during the course of the procedure as will be described below.

Suitable sources of viral proteins which can be employed in conjunction with the method of the invention include Sendai, influenza, herpes simplex or genitalis, HTLV I, II or III, retroviruses, pox virus, respiratory syncytial virus, toga virus, and the like. The present invention can also be employed in conjunction with membrane proteins derived from bacterial or parasitic organisms such as for example organisms causing malaria, chlamydia, N. gonorrhea, salmonella, liver flukes and the like.

Peptides or proteins having at least enough hydrophobic character to allow for association with a lipid bilayer are preferred. Additionally, the peptides or proteins can be covalently cross-linked to a lipid as described in *Liposome Technology*, 2nd Edition, Vol. II, Entrapment of Drugs and Other Materials, edited by Gregory Gregoriadis, (CRC Press, Boca Raton, Ann Arbor, London, Tokyo), Chapter 10, pages 167–184 (1993).

Examples of suitable peptides and proteins can be found in the following references:

(1) G. Goodman-Snitkoff et al., Defining Minimal Requirements for Antibody Production to Peptide Antigens, *Vaccine*, Vol. 8, page 257 (1990);

(2) G. Goodman-Snitkoff et al., Role of Intrastructural/Intermolecular Help in Immunization with Peptide-Phospholipid complexes, *J. Immunol.*, Vol. 147, page 410 (1991);

(3) R. J. Mannino et al., Liposomes as Adjuvants for Peptides: Preparation and Use of Immunogenic Peptide-phospholipid Complexes, in Liposome Technology, 2nd Edition, Vol. II, Entrapment of Drugs and other Materials, edited by Gregory Gregoriadis, (CRC Press, Boca Raton, Ann Arbor, London, Tokyo), Ch. 10, pp. 167–184 (1993).

The aforesaid peptides or proteins, or mixtures thereof to provide multiple epitopes, are then mixed with phospholipid to form protein- or peptide-cochleates. Carbohydrate or DNA immunogen can also be added.

In order to form cochleate precipitates, a majority of the lipid present must be negatively charged. One type of lipid can be used or a mixture of lipids can be used. Phosphatidylserine or phosphatidyl-glycerol have generally been used. Phosphatidyl-inositol also forms a precipitate which converts to liposomes upon contact with EDTA. A substantial proportion of the lipid can, however, be neutral or positively charged. The present inventors have included up to 40 mol % cholesterol based on total lipid present and routinely make protein-lipid cochleates which contain 10 mol % cholesterol and 20% viral membrane lipids. Phosphatidylethanolamine, plain or cross-linked to peptides or proteins, can also be incorporated into cochleates.

While negatively charged lipid can be used, a negatively charged phospholipid is preferred, and of these phosphatidylserine, phosphatidylinositol, phosphatidic acid, and phosphatidylglycerol are most preferred.

One skilled in the art can readily determine how much lipid must be negatively charged by preparing a mixture with known concentrations of negative and non-negative lipids and by any of the procedures described below, determining whether precipitates form.

Figure 4:
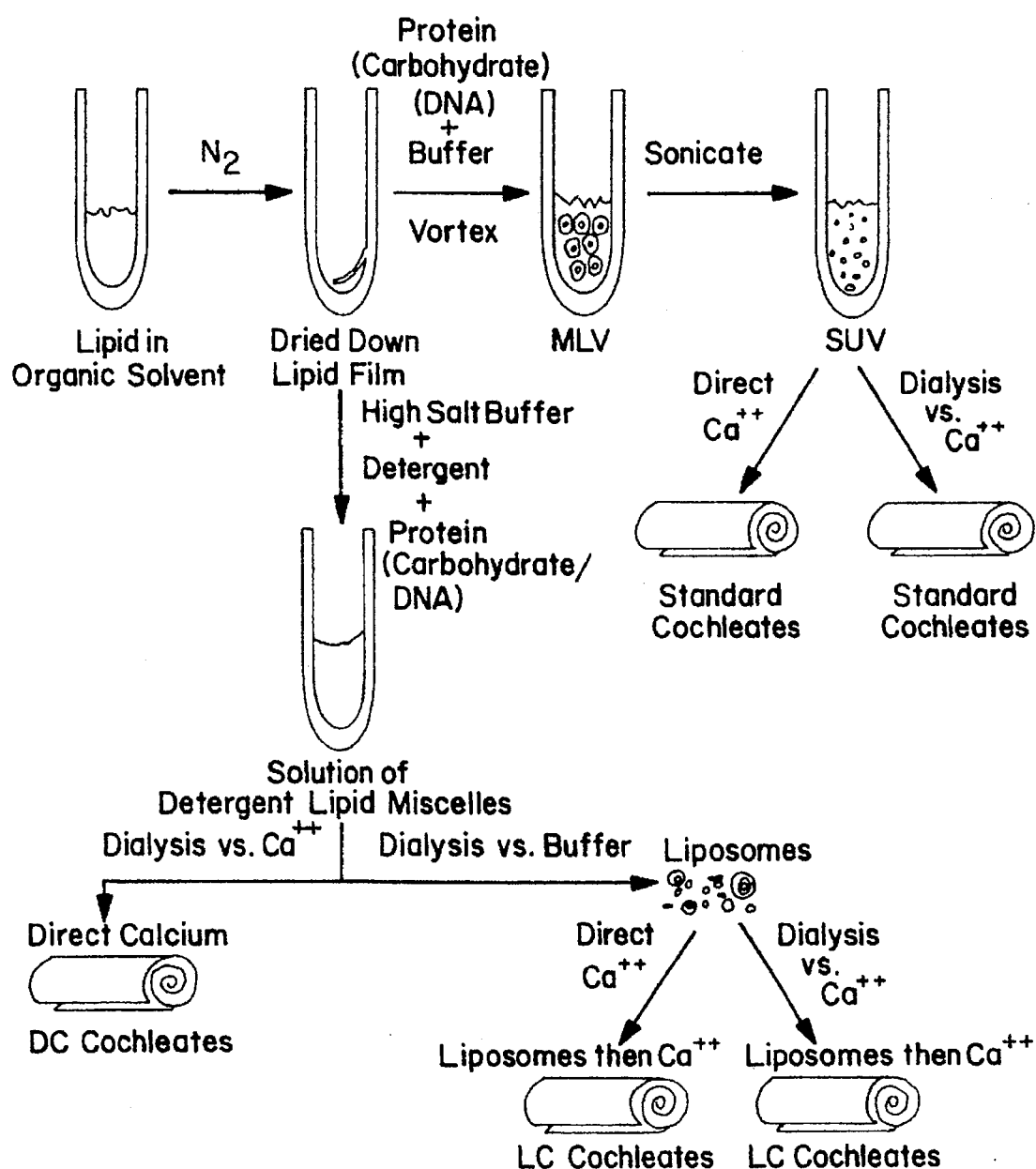
FIG. 4 summarizes the various alternative procedures for the preparation of protein- or peptide-cochleates.

There are several known procedures for making the protein- or peptide-cochleates of the present invention and these are schematized in FIG. 4. One such method is the so-called standard cochleate obtained by use of the calcium-EDTA-chelation technique described by D. Papahadjopoulos et al. {*Biochem. Biophys. Acta*, Vol. 394, page 483 (1975)} for making plain phospholipid cochleates. In an embodiment of the present invention, a modification of such procedure is employed. In the modified procedure a negatively charged lipid such as phosphatidylserine, phosphatidylinositol, phosphatidic acid or phosphatidylglycerol in the absence or presence of cholesterol (up to 3:1, preferably 9:1 w/w) are utilized to produce a suspension of multilamellar protein lipid vesicles containing and surrounded by antigen (protein, carbohydrate, and/or DNA) which are converted to small unilamellar protein lipid vesicles by sonication under nitrogen. These vesicles are dialyzed at room temperature against buffered divalent cation, e.g., calcium chloride, resulting in the formation of an insoluble precipitate referred to as a cochleate cylinder. After centrifugation, the resulting pellet can be taken up in buffer to yield the cochleate solution utilized in the vaccine of the present invention.

In an alternative and preferred embodiment, an amount of negatively charged lipid, e.g., phosphatidylserine, and cholesterol in the same proportions as above and equal to from about 1 to 10 times the weight, preferably equal to four times the weight of the viral or other additional lipids are utilized to prepare the cochleates. Supernatant from the nonionic detergent extraction of membrane proteins or other proteins or peptides is then added, and the solution is vortexed for five minutes. Either carbohydrates or DNA can be used in place of or in combination with peptides or proteins. This solution is then dialyzed against buffered divalent cation, e.g., calcium chloride, to produce a precipitate which can be called a DC (for direct calcium dialysis) cochleate.

An additional, related method for reconstituting proteins or peptides into cochleates has been developed and is called the LC method (liposomes before cochleates). The initial steps involving addition of extracted protein or peptide, or carbohydrate, or DNA or combinations thereof, to dried down negatively charged lipid and cholesterol are the same as for the DC method. However, the solution is next dialyzed against buffer (e.g., 2 mMTES, 2 mML-histidine, 100 mMNaCl, pH 7.4) to form small liposomes containing the glycoproteins, peptides, DNA, and/or carbohydrates. A divalent cation, e.g., calcium, is then added either directly or by dialysis to form a precipitate which consists of protein- or peptide-cochleates.

In the above procedures for making the cochleates of the present invention, the divalent cation can be any divalent cation that can induce the formation of a cochleate or other insoluble lipid-antigen structures. Examples of suitable divalent cations include $Ca^{++}$, $Mg^{++}$, $Ba^{++}$, and $Zn^{++}$ or other elements capable of forming divalent ions or other structures having multiple positive charges capable of chelating and bridging negatively charged lipids.

Protein- or peptide-cochleates can be lyophilized and stored at room temperature for indefinitely or can be stored in a divalent cation-containing buffer at 40° C. for at least six months.

After the protein- or peptide-cochleate precipitate is formed, the vaccine is made by diluting into an appropriate pharmaceutically acceptable carrier (e.g., a divalent cation-containing buffer).

The reconstituted viral, bacterial, parasitic or animal proteins, peptides, carbohydrates, and/or DNA in the cochleates of the present invention can be employed as vaccines to render immunity to hosts treated with such compositions.

Cochleate vaccines can include multiple synthetic peptide epitopes and thus offer a simple means of generating antiviral cell-mediated immunity in a genetically heterogeneous population. Formulations can be generated using mixtures of proteins or peptides either individually or as mixtures in various ratios.

According to the method of the present invention, a host is immunized by administering an immunologically effective amount of the above-described protein- or peptide-cochleates. Advantageously, administration may be oral. However, the vaccine can also be administered by any of a variety of art-recognized modes of administration, including intramuscular, subcutaneous, intradermal, intranasal, intra-ocular, intraperitoneal, intra-vaginal, intra-rectal and by lung aerosol. Appropriate dosages are determinable by, for example, dose-response experiments in laboratory animals or in clinical trials and taking into account body weight of the patient, absorption rate, half life, disease severity and the like. The number of doses, daily dosage and course of treatment may vary from individual to individual.

Pharmaceutical formulations can be of solid form including tablets, capsules, pills, bulk or unit dose powders and granules or of liquid form including solutions, fluid emulsions, fluid suspensions, semisolids and the like. In addition to the active ingredient, the formulation would comprise suitable art-recognized diluents, carriers, fillers, binders, emulsifiers, surfactants, water-soluble vehicles, buffers, solubilizers and preservatives.

The skilled artisan can determine the most efficacious and therapeutic means for effecting treatment practicing the instant invention. Reference can also be made to any of numerous authorities and references including, for example, "Goodman & Gilman's, The Pharmaceutical Basis for Therapeutics", (6th Ed., Goodman, et al., eds., MacMillan Publ. Co., New York, 1980).

The vaccines elicit humoral (antibody) and cell mediated (proliferation of helper T cells or cytotoxic "killer" activity by cytotoxic cells)—circulating and mucosal protective immune responses as shown in the examples below.

EXAMPLES

The present invention will now be described by means of specific examples which are not meant to limit the invention.

EXAMPLE 1

FORMATION OF PROTEIN-COCHLEATES USING SENDAI OR INFLUENZA VIRUSES

Materials and Methods

Materials. Bovine brain phosphatidylserine in chloroform was purchased from Avanti Polar Lipids, Birmingham, Ala. in glass ampules and stored under nitrogen at −20° C. Cholesterol (porcine liver) grade I, β-D-octyl-glucopyranoside, fluorescein isothiocyanate (FITC)-dextran (average mol. wt. 67,000), metrizamide grade I, and chemicals for buffers and protein and phosphate determinations, were obtained from Sigma Chemical Company, St. Louis, Mo. Organic solvents were purchased from Fisher Scientific Co., Fairlawn, N.J. Reagents for polyacrylamide gel electrophoresis were from BioRad Laboratories, Richmond, Calif. S1000 Sephacryl Superfine was obtained from Pharmacia, Piscataway, N.J. Thick walled polycarbonate centrifuge tubes (10 ml capacity) from Beckman Instruments, Palo Alto, Calif., were used for vesicle preparations, washes, and gradients. A bath type sonicator, Model G112SP1G, from Laboratory Supplies Company, Hicksville, N.Y. was used for sonications.

Viral Growth and Purification. Virus was grown and purified essentially as described by M. C. Hsu et al., Virology, Vol. 95, page 476 (1979). Sendai (parainfluenza type I) and influenza (A/PR8/34) viruses were propagated in the allantoic sac of 10 or 11 day old embryonated chicken eggs. Eggs were inoculated with 1–100 egg infectious doses ($10^3$ to $10^5$ viral particles as determined by HA titer) in 0.1 ml of phosphate buffered saline (0.2 gm/L KCl, 0.2 gm/L $KH_2PO_4$, 8.0 gm/L NaCl, 1.14 gm/L $Na_2H$-$PO_4$, 0.1 gm/L $CaCl_2$, 0.1 gm/L $MgCl_2 6H_2O$ (pH 7.2)). Eggs were incubated at 37° C. for 48 to 72 hours, followed by incubation at 4° C. for 24 to 48 hours. Allantoic fluid was collected and clarified at 2,000 rpm for 20 minutes at 5° C. in a Damon IEC/PR-J centrifuge. The supernatant was then centrifuged at 13,000 rpm for 60 minutes. This and all subsequent centrifugations were performed in a Sorvall RC2-B centrifuge at 5° C. using a GG rotor. The pellets were resuspended in phosphate buffered saline (pH 7.2) by vortexing and sonicating, followed by centrifugation at 5,000 rpm for 20 minutes. The pellet was resuspended by vortexing and sonicating, diluting, and centrifuging again at 5,000 rpm for 20 minutes. The two 5,000 rpm supernatants were combined and centrifuged at 13,000 rpm for 60 minutes. The resulting pellets were resuspended in phosphate-buffered saline by vortexing and sonicating, aliquoted, and stored at −70° C. Sterile technique and materials were used throughout viral inoculation, isolation, and purification.

Extraction of Viral Glycoproteins and Lipids. Virus stored at −70° C. was thawed, transferred to sterile thick-walled polycarbonate tubes, and diluted with buffer A (2 mMTES, 2 mML-histidine, 100 mM NaCl (pH 7.4)). It was pelleted at 30,000 rpm for 1 hour at 5° C. in a Beckman TY65 rotor. The supernatant was removed and the pellet resuspended to a concentration of 2 mg viral protein per ml of extraction buffer (2M NaCl, 0.02M sodium phosphate buffer (pH 7.4)) by vortexing and sonicating. The nonionic detergent β-D-octyl-glucopyranoside was then added to a concentration of 2% (w/v). The suspension was mixed, sonicated for 5 seconds, and placed in a 37° C. water bath for 45 minutes. At 15, 30, and 45 minute incubation times, the suspension was removed briefly for mixing and sonication. Nucleocapsids were pelleted by centrifugation at 30,000 rpm for 45 minutes in a TY65 rotor. The resulting clear supernatant was removed and used in the formation of viral glycoprotein-containing cochleates. Some modification of the above procedure may have to be employed with other membrane proteins. Such modifications are well known to those skilled in the art.

Formation of Cochleares

A. Standard Cochleates

Large, unilamellar, non protein-containing, phospholipid vesicles were made by a modification of the calcium-EDTA-chelation technique described by D. Papahadjopoulos et al., *Biochem. Biophys. Acta*, Vol. 394, page 483 (1975). Phosphatidylserine and cholesterol (9:1 wt ratio) were dried down in a clean glass tube under a stream of nitrogen. The lipid was resuspended in buffer A (pH 7.4) to a concentration of 6 μMol/ml by vortexing for 7 minutes. The resulting suspension of multilamellar vesicles was converted to small unilamellar vesicles by sonication under nitrogen at 5°–10° C for approximately 20 minutes in a bath-type sonicator. (Model G1125P16, Laboratory Supplies Co., Hicksville, N.Y.). These vesicles were dialyzed at room temperature against two changes of 250 ml of buffer A (pH 7.4) with 3 mM $CaCl_2$. This results in the formation of an insoluble precipitate referred to as cochleate cylinders.

B. DC Cochleates

The envelope glycoproteins of Sendai virus account for about 33% of the total viral protein and are present in approximately equal weight to the viral lipid. An amount of phosphatidylserine and cholesterol (9:1 wt ratio) equal to 4 times the weight of the viral lipid was dried down under nitrogen in a clean glass tube. The amount of lipid added to the influenza virus extract was also equal to four times of the total viral protein. Supernatant from β-D-octyl-glucopyranoside-extracted virus (see Extraction of Viral Glycoproteins and Lipids) was added, and the solution was vortexed for 5 minutes. The clear, colorless solution which resulted was dialyzed at room temperature against three changes (minimum 4 hours per change) of buffer A (2 mM TES N-Tris[hydroxymethyl]-methyl-2 aminoethane sulfonic acid, 2 mM L-histidine, 100 mM NaCl, pH 7.4) containing $3mMCaCl_2$. The final dialysis routinely used is 6 mM $Ca^{2+}$, although 3 mM $Ca^{2+}$ is sufficient and other concentrations may be compatible with cochleate formation. The ratio of dialyzate to buffer for each change was a minimum of 1:100. The resulting white calcium-phospholipid precipitates have been termed DC cochleates. When examined by light microscopy (×1000, phase contrast, oil), the suspension contains numerous spheres up to several microns in diameter with bumps or spikes on their surface, as well as needle-like structures.

C. LC Cochleates

Solubilized viral envelope was added to a film of phosphatidylserine and cholesterol (9:1 w/w) equal to four times the weight of the viral glycoproteins (which comprise one-third of the total protein of the virus), and then vortexed. This detergent solution containing solubilized lipids and membrane proteins was first dialyzed overnight using a maximum ratio of 1:200 (v/v) of dialysate to buffer A without divalent cations, followed by three additional changes of buffer leading to the formation of small protein lipid vesicles. These vesicles were converted to a protein- or peptide-cochleate precipitate, either by the direct addition of $Ca^{2+}$ ions, or by dialysis against one change of buffer A containing 3 mM $Ca^{2+}$ ions, followed by one containing buffer A with 6 mM $Ca^{2+}$.

EXAMPLE 2

CIRCULATING ANTIBODY RESPONSES TO ORALLY DELIVERED PROTEIN-COCHLEATE VACCINES

In order to make the vaccine, influenza virus was grown, purified, and the glycoproteins and lipids extracted and isolated as described in Example 1. Protein-cochleates were made according to the "LC cochleate" procedure described above.

Figure 5A:
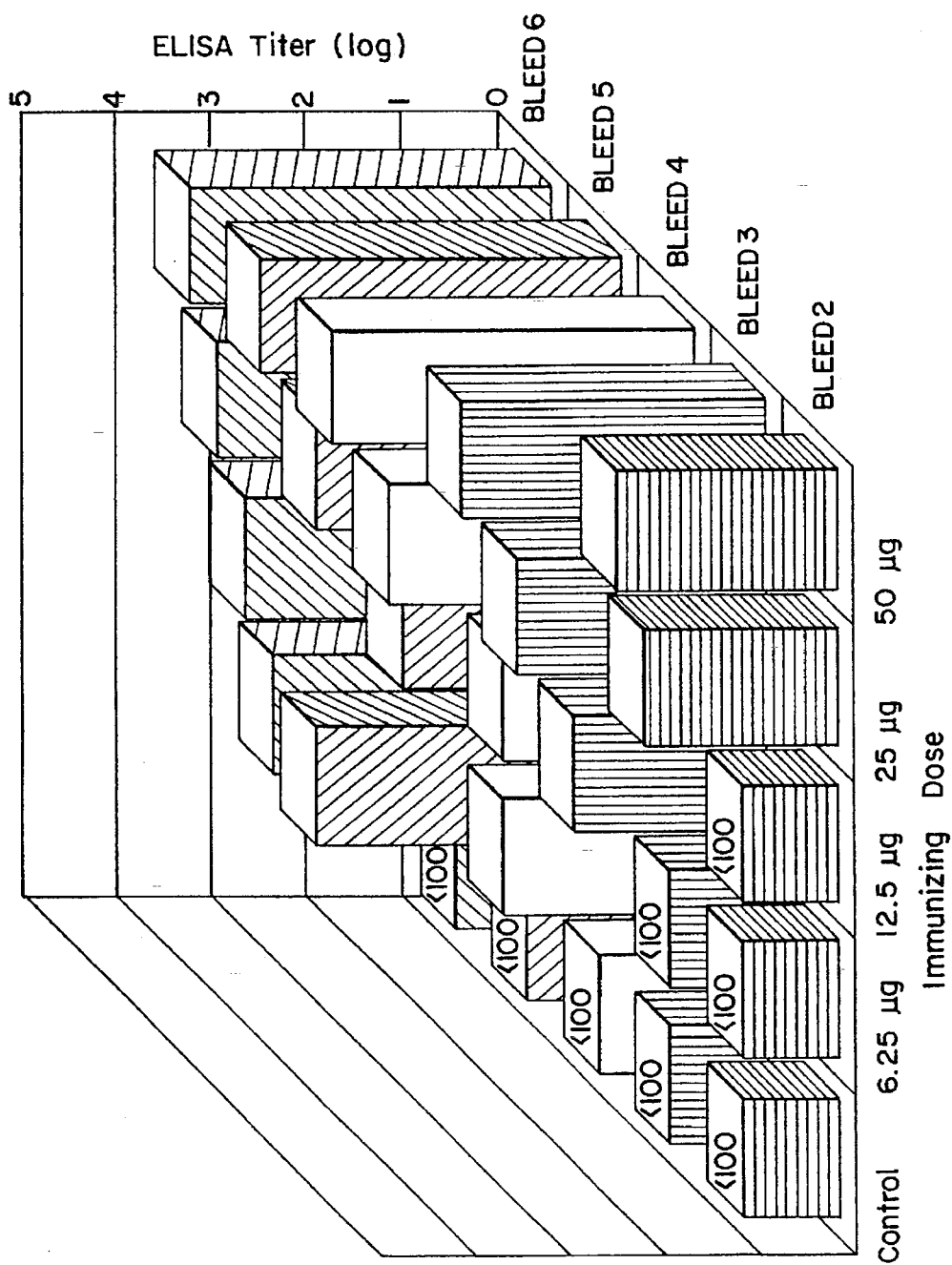
FIGS. 5(A) and 5(B) show serum antibody titers in mice following oral administration of influenza protein-cochleates.

Cochleate vaccines containing the glycoproteins and lipids from the envelope of influenza virus and phosphatidylserine and cholesterol were given to mice by gradually dispensing 0.1 ml liquid into the mouth and allowing it to be comfortably swallowed. FIGS. 5(A) (from Experiment A) and 5(B) (from Experiment B) show resulting total circulating antibody levels specific for influenza glycoproteins, as determined by ELISA. Antibody titer is defined as the highest dilution that still gives the optimal density of the negative control.

In Experiment A that generated the data shown in FIG. 5(A), initial vaccine doses of 50, 25, 12.5 or 6.25 μg of glycoproteins (groups 1 through 4 respectively) were administered at 0 and 3 weeks. The third and fourth immunizations (6 and 19 weeks) were at one fourth the dose used for the initial two immunizations. Bleed 1–Bleed 6 occurred at 0, 3, 6, 9, 19, and 21 weeks. The data demonstrate that high circulating antibody titers can be achieved by simply drinking cochleate vaccines containing vital glycoproteins. The response is boostable, increasing with repeated administration, and is directly related to the amount of glycoprotein in the vaccine.

Figure 5B:
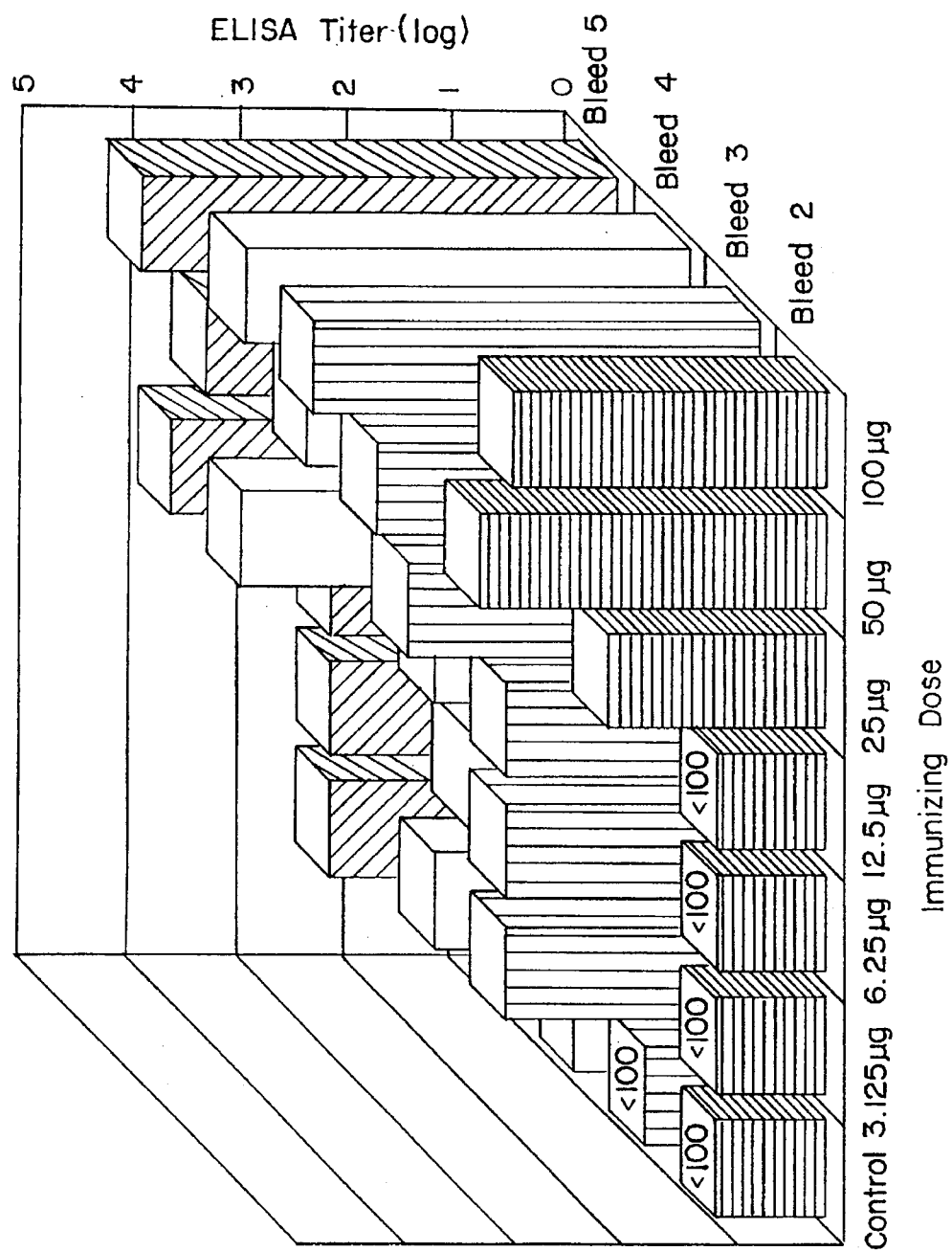

These observations were confirmed and extended in Experiment B that generated the data shown in FIG. 5(B). The dose range was expanded to include 100 µg and 3.1 µg initial doses. Vaccine was given at 0, 3 and 15 weeks, with the third immunization at one fourth the dose of the initial two. Bleed 1 to Bleed 6 occurred at 0, 3, 6, 15 and 16 weeks. Circulating influenza glycoprotein-specific responses were detectable after a single administration for the top five doses, and for all groups after two feedings. The data shown is for pooled sera from each group, but all mice given the four highest doses, and four of five mice in groups five and six, responded to the vaccine with circulating antibody titers ranging from 100 to 102,400. Group seven, which received no vaccine, had titers less than 50 for all mice at all time points.

The antibody response is long lived. Titers 13 weeks after the third immunization (FIG. 5(A), bleed 5) and 12 weeks after the second immunization (FIG. 5(B), bleed 4) remained the same or within one dilution higher or lower than seen at 3 weeks after the previous boost.

In Experiment C that generated the data shown in FIG. 6, a single oral dose of 50 µg was administered. The mice were bled at 0, 28, 56 and 90 days and the antibody titer was determined by ELISA. The slowly increasing titers shown in FIG. 6 indicate the possibility of persistence and slow release of antigen from the cochleates.

EXAMPLE 3

PROTECTION FROM INTRANASAL CHALLENGE WITH LIVE INFLUENZA FOLLOWING ORAL IMMUNIZATION WITH GLYCOPROTEIN-COCHLEATES

In order to determine whether oral administration of the subunit vaccine described in Example 2 could lead to protective immunity in the respiratory tract, the mice described in Experiment B of Example 2 were immunized with cochleates at 0, 3, and 15 weeks. The immunized mice were challenged by intranasal application of $2.5 \times 10^9$ particles of influenza virus at 16 weeks. Three days after viral challenge, mice were sacrificed, and lungs and trachea were obtained. The entire lung or trachea was triturated and sonicated, and aliquots were injected into embryonated chicken eggs to allow amplification of any virus present. After three days at 37° C., allantoic fluid was obtained from individual eggs, and hemagglutination (HA) titers were performed.

Mice were also challenged with live influenza intranasally following oral cochleate administration in Experiment A of Example 2. Lungs were obtained three days later and cultured to detect presence of virus.

The combined data for the two experiments is given in Table 1. These results are also shown graphically in FIG. 7.

TABLE 1

| Vaccine Dose µg Protein | Trachea[1] # Infected/ Total | Lungs[2] # Infected/ Total | Lungs[3] # Infected/ Total |
| --- | --- | --- | --- |
| 100 | 0/5 | 0/5 | 0/5 |
| 50 | 2/5 | 0/5 | 2/10 |
| 25 | 0/5 | 0/5 | 1/10 |
| 125 | 1/5 | 0/5 | 1/10 |
| 6.25 | 0/5 | 5/5 | 6/10 |
| 3.12 | 4/5 | 5/5 | 5/5 |
| 0 | 5/5 | 5/5 | 9/10 |

[1]Mice from Experiment B.
[2]Mice from Experiment B.
[3]Mice from Experiments A and B.

The data in Table 1 shows that all five of the unvaccinated mice had sufficient virus in the trachea to infect the embryonated chicken eggs (greater than $10^3$ particles per trachea or at least one egg infectious dose (EID) per 0.1 ml of suspension). In contrast, the oral vaccine provided a high degree of protection from viral replication in the trachea. All mice in groups 1, 3 and 5 of Experiment B were negative for virus. Two mice in group 2, 1 in group 4, and 4 in group 6 (the lowest vaccine dose) of Experiment B had sufficient virus to test positive in this very sensitive assay used to detect presence of virus.

The oral protein cochleate vaccine also provided protection against viral replication in the lungs. All twenty mice which received the four highest doses of vaccine were negative for virus when lung suspensions were cultured in embryonated chicken eggs (Table 1). All mice in the groups immunized with 6.25 µg and 3.1 µg glycoproteins and all mice in the unvaccinated control were positive for virus.

Even in the lowest two vaccine doses, there was some inhibition of viral replication. When lung suspensions were diluted 1/10 and inoculated into eggs, only one animal in the groups immunized with 6.25 µg was positive, as compared to three in the groups immunized with 3.12 µg and three in the unvaccinated control. Culturing of 1/100 dilutions resulted in one positive animal in each of the groups immunized with 6.25 and 3.12 µg, but 3 of 5 remained positive in the unvaccinated group. In addition, for the two animals in the group that was immunized with 3.12 µg, but which were negative at 1/100, only 50% of the eggs were infected at 1/10 and had low HA titers. In contrast, for the unvaccinated group, all eggs were infected and produced maximal amounts of virus at 1/10 and 1/100 dilutions.

EXAMPLE 4

ORAL ADMINISTRATION OF SENDAI COCHLEATE STIMULATES CIRCULATING ANTIBODY PRODUCTION

Figure 8:
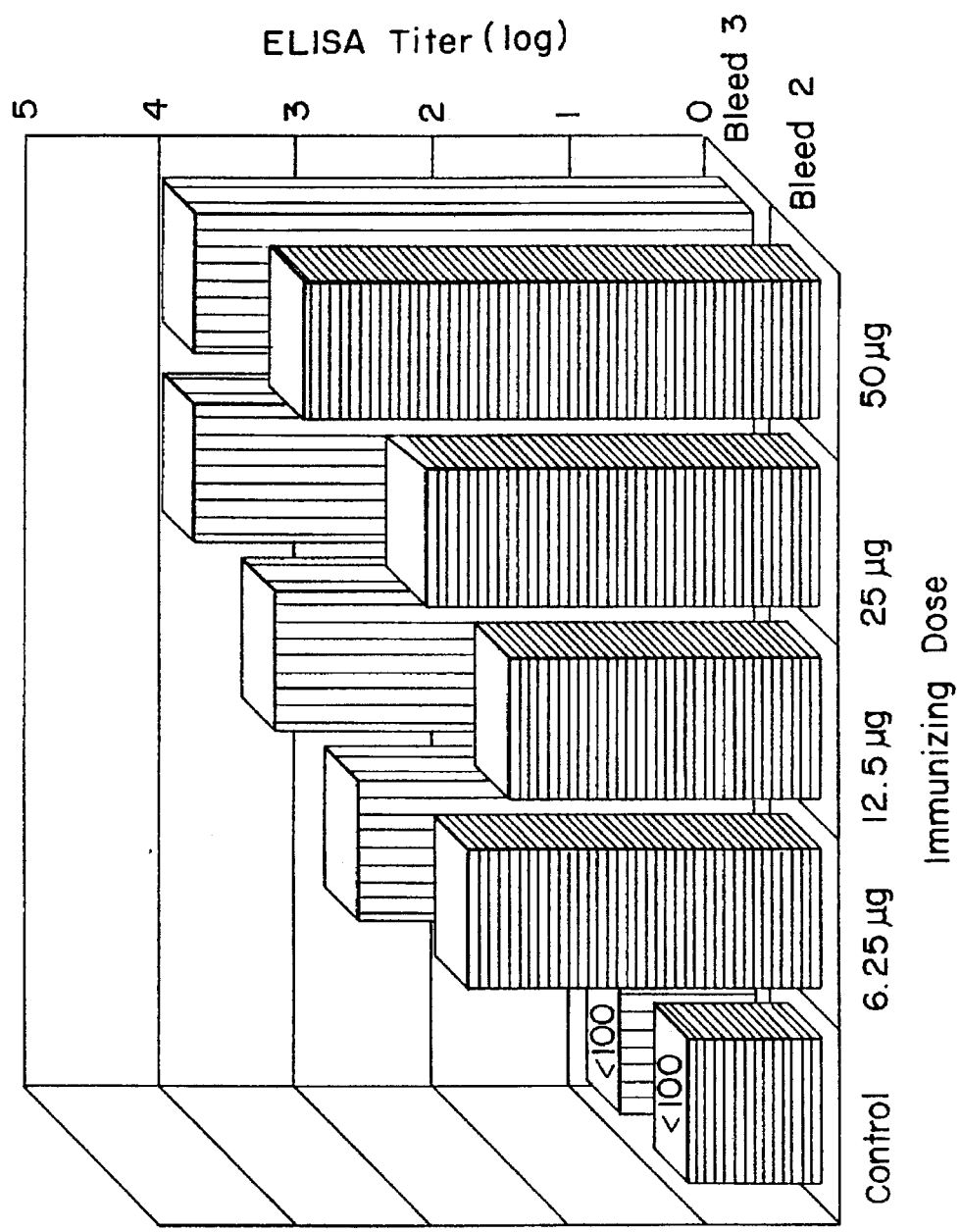
FIG. 8 is a graphic representation of serum antibody titers in mice following oral administration of Sendai-cochleates.

C57BL6 mice were given cochleates containing Sendai virus glycoproteins orally at 0 and 3 weeks. They were bled at 0 (bleed 1), 3 (bleed 2), and 6 (bleed 3) weeks. Group 1 received approximately 50 µg protein, Group 2 about 25 µg, Group 3 about 12.5 µg, Group 4 about 6.25 µg, and Group 5 (negative control) received 0 µg protein. The levels of Sendai specific antibodies in the serum pooled from 5 mice in each dose group were determined by ELISA. The results are shown in FIG. 8. It can be seen that strong antibody responses were generated, that the magnitude of the response was directly related to the immunizing dose, and that the magnitude of the response increased (boosted) after a second immunization.

Figure 9:
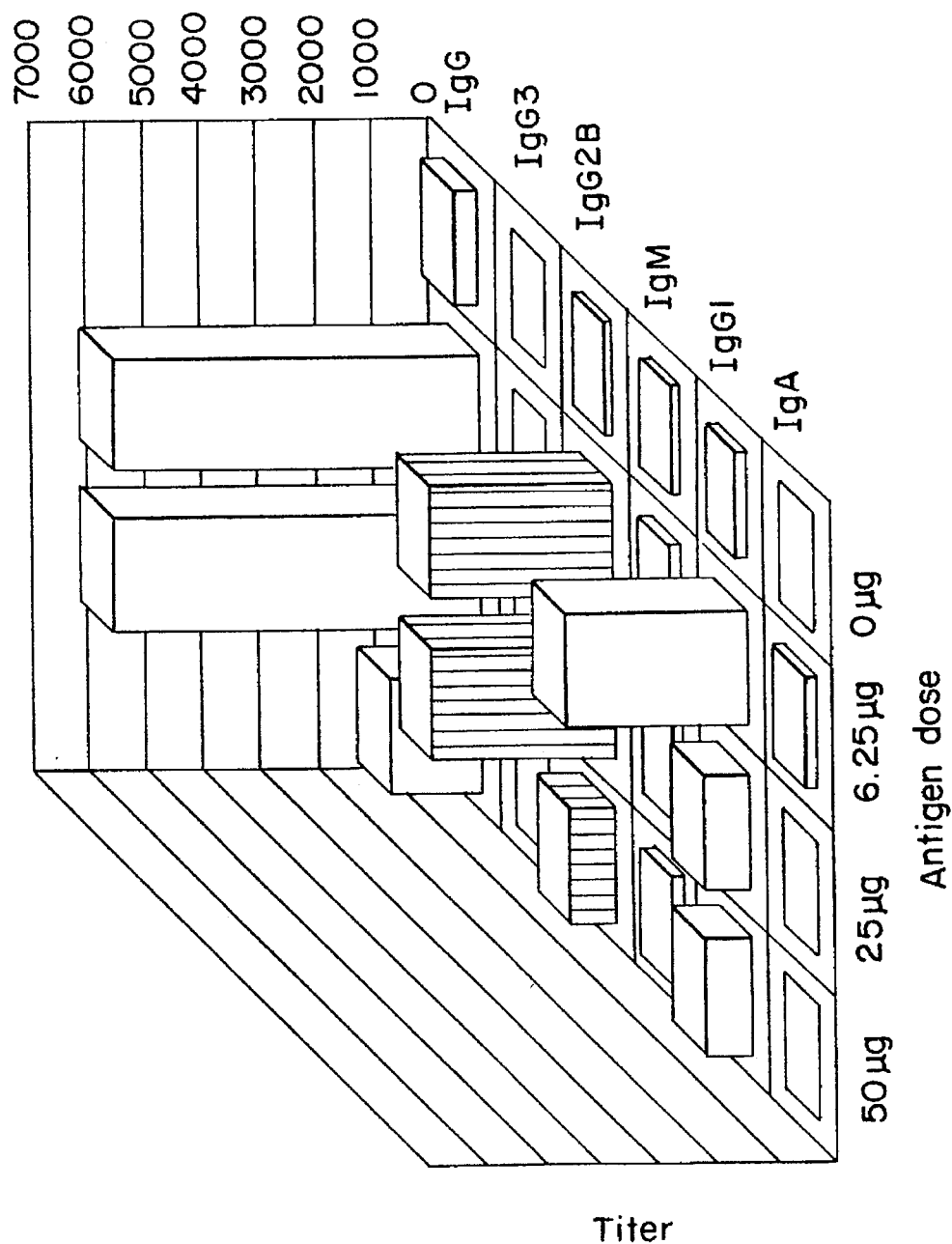
FIG. 9 is a graph showing antibody-isotypes following oral administration of Sendai protein cochleates.
Figure 10:
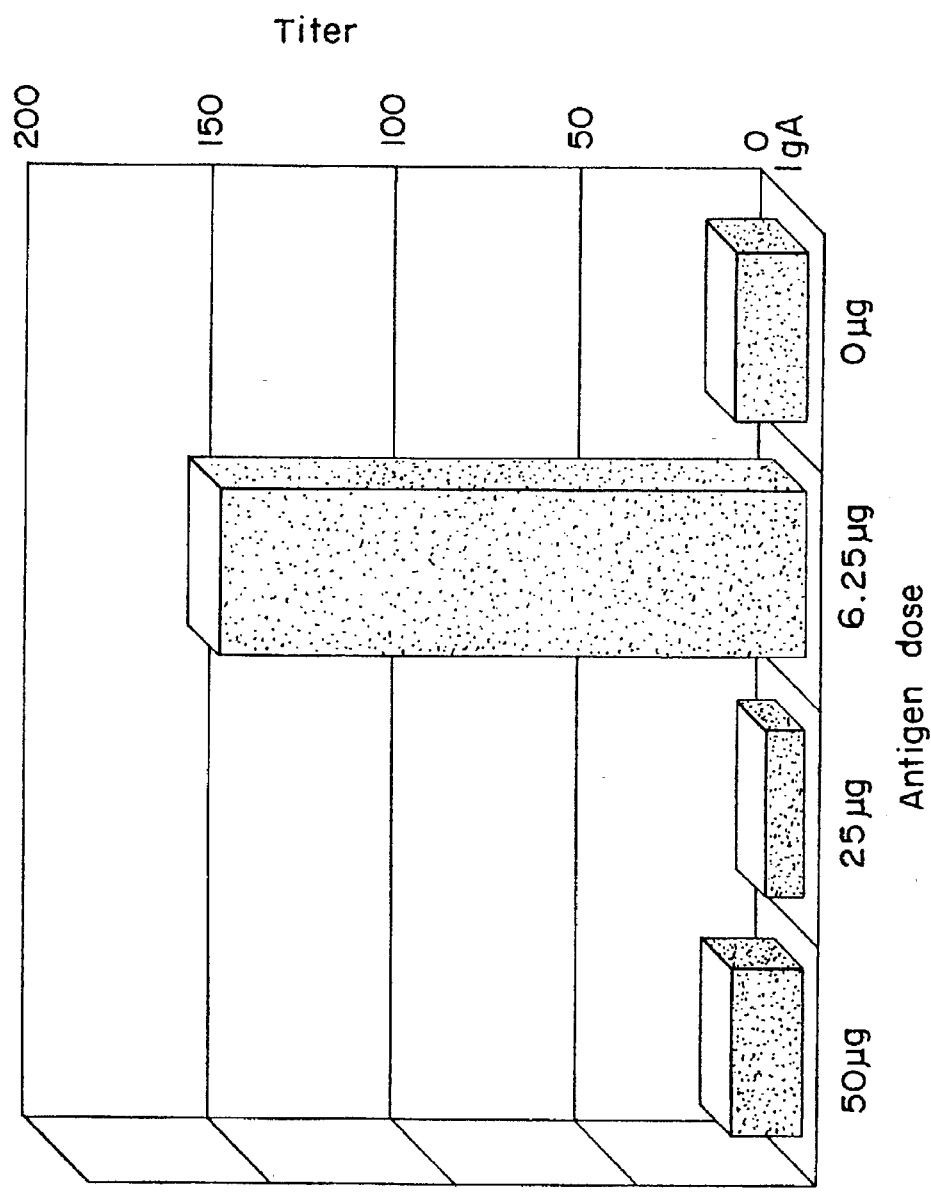
FIG. 10 is a graph showing antigen-specific IgA following oral administration of Sendai protein cochleates.

The response was extremely long-lived. FIG. 9 shows a breakdown of the classes and subtypes of Sendai-glycoprotein-specific antibodies still circulating 8 months later. The response is predominantly IgG, indicative of the involvement in T cell help and establishment of long-term memory cells associated with a secondary immune response. Surprisingly, the lowest dose which initially had the lowest response, now had the highest circulating antibody levels. This may be due to the immune system's down regulation of the very high responses originally but allowing the low response to slowly climb. This may also indicate a persistence and slow release of antigen. It is also interesting and consistent with the use of the oral route of immunization that significant IgA titers are generated and maintained (FIG. 10).

EXAMPLE 5

IMMUNIZATION WITH PROTEIN-COCHLEATES LEADS TO PRODUCTION OF ANTIGEN-SPECIFIC LOCAL OR SECRETORY IgA

Figure 11:
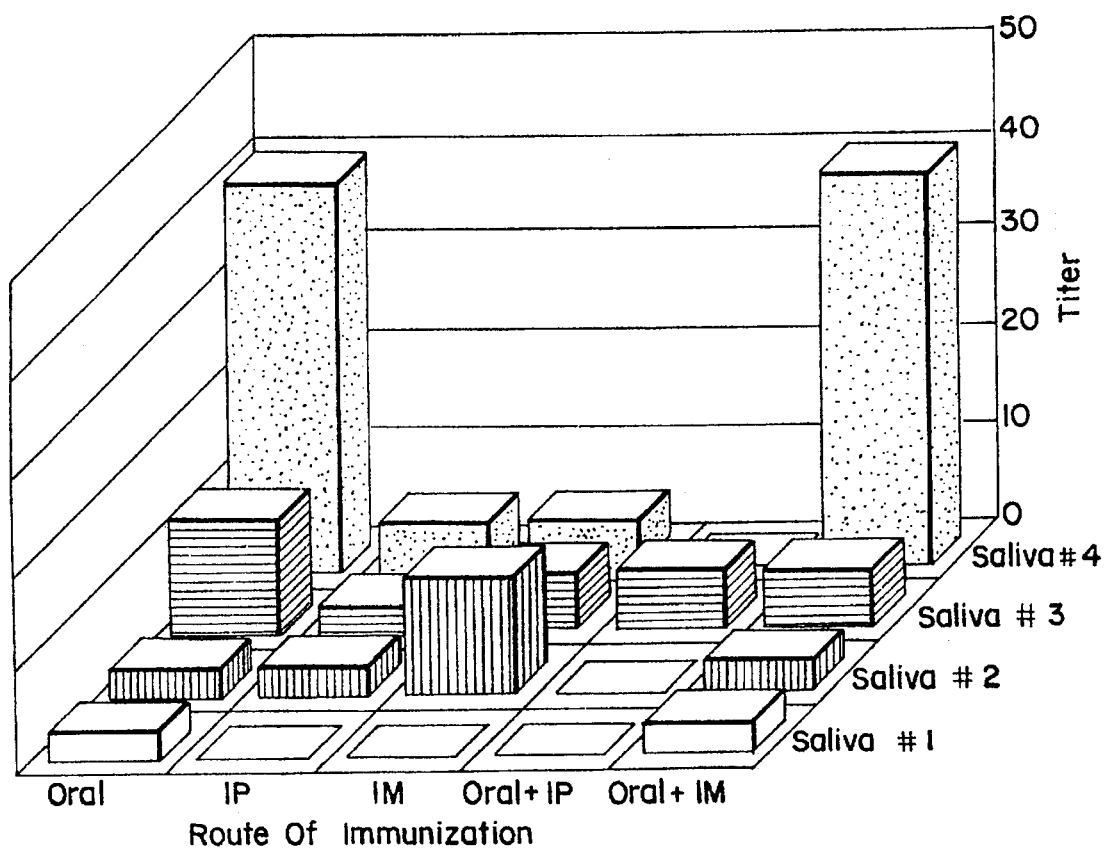
FIG. 11 is a graph showing the production of antigen-specific local or secretory IgA after three immunizations with protein-cochleates.

Balb C mice were given Sendai glycoprotein-containing cochleates (50 µg dose) by a single route or two routes simultaneously. They were boosted using the same immunization protocol at 3 weeks. Saliva one was also 3 weeks after the primary immunization. Saliva two was one week, and three was 3 weeks after the second immunization. They were all boosted by oral administration at 24 weeks and saliva four was taken one week later. As can be seen in FIG. 11, the oral route and oral plus IM routes generated the highest salivary IgA titers. Demonstration of such high mucosal antibody titers following oral immunization is of considerable significance and highly desired for protection against organisms invading through mucosal surfaces.

EXAMPLE 6

PROLIFERATIVE RESPONSES ARE GENERATED TO ANTIGENS CONTAINED IN COCHLEATES

Figure 12A:
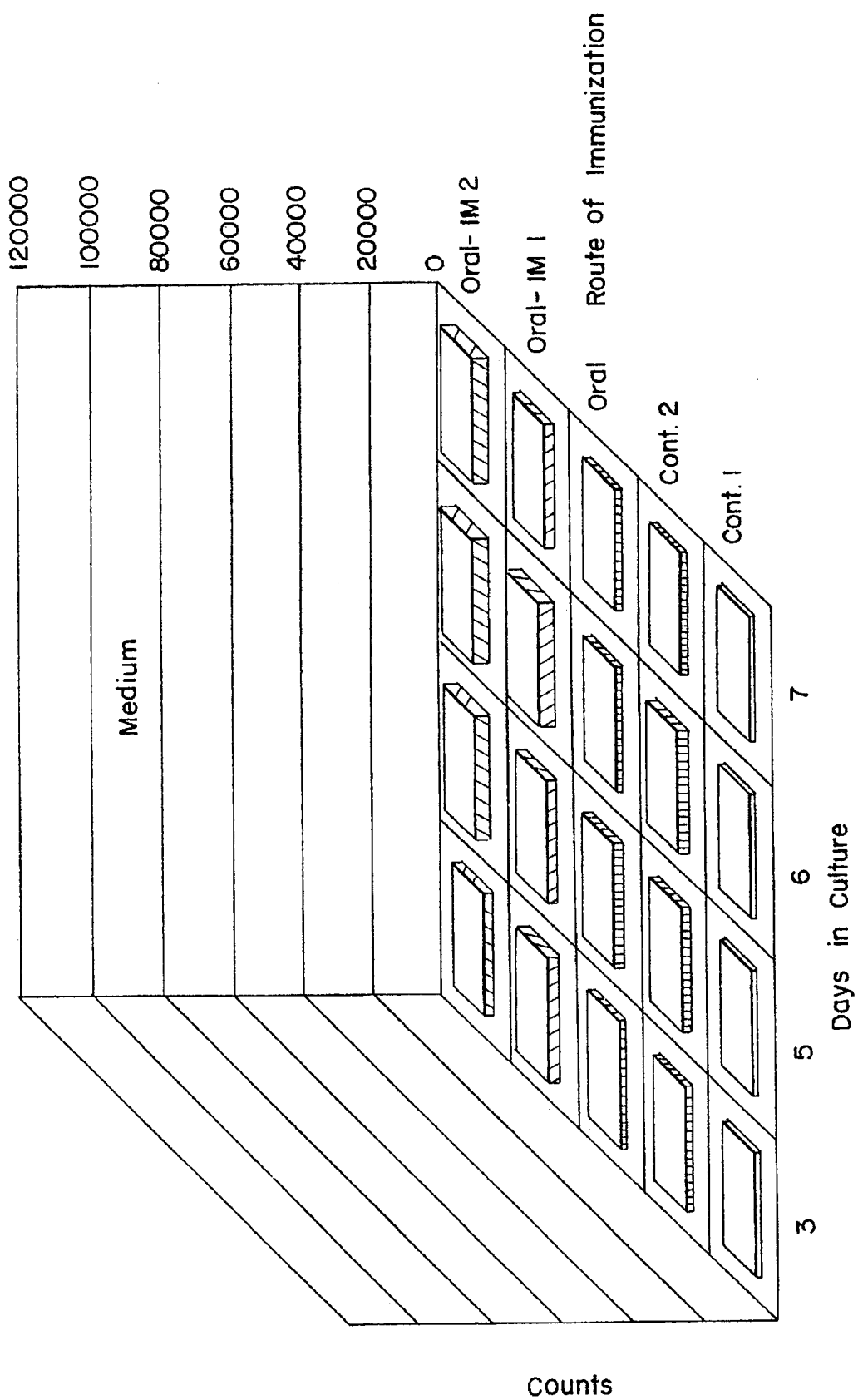
FIGS. 12(A) and (B), 13(A) and (B), 14(A) and (B), 15(A) and (B), and 16(A) and (B) show spleenocite proliferation following immunization with influenza-cochleates. Part (A) of each figure shows the response to media as a control. Part (B) of each figure shows the proliferative response to ultraviolet light-inactivated influenza virus over several days in culture.
Figure 12B:
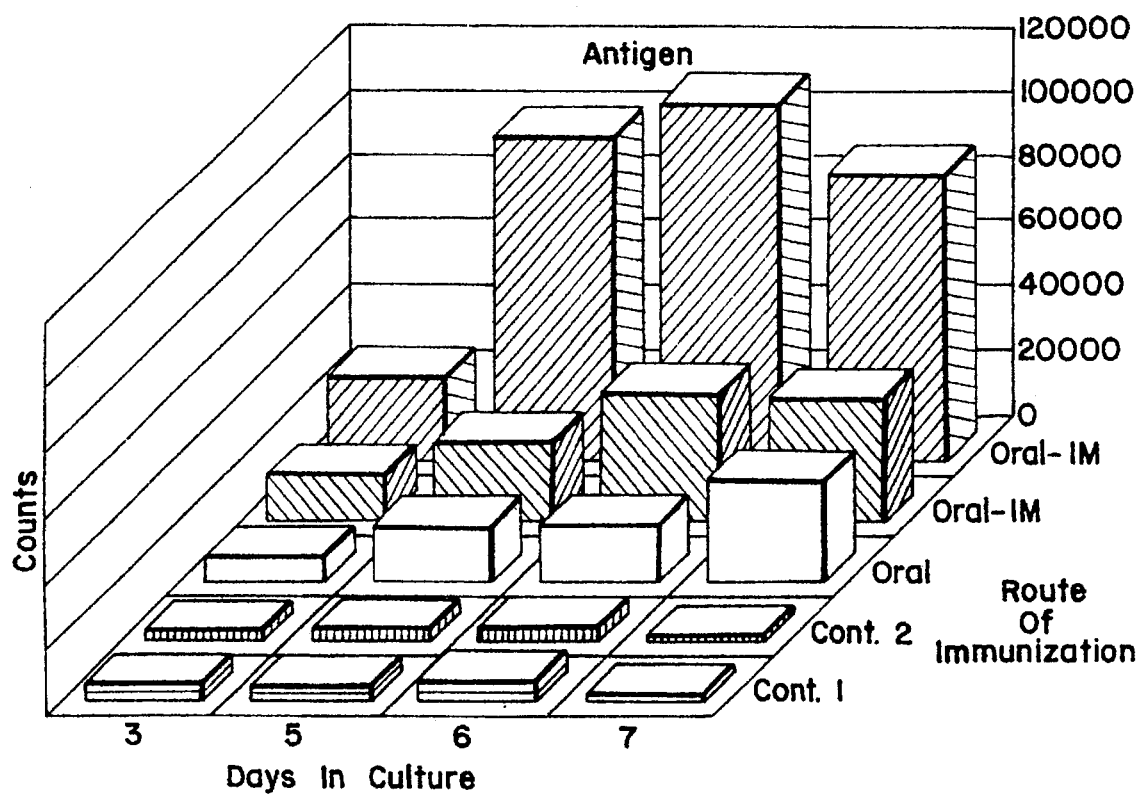
Figure 13A:
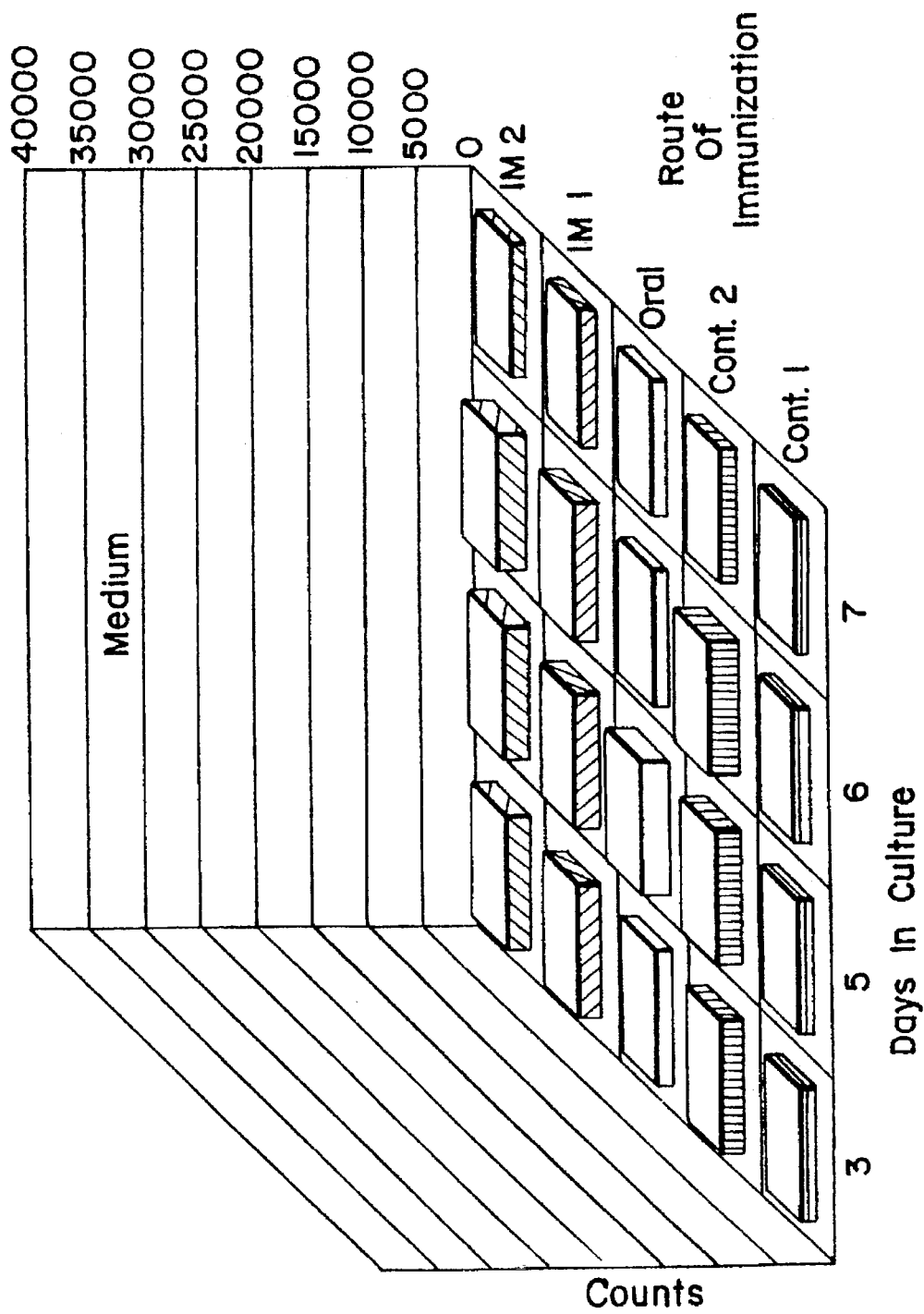
Figure 13B:
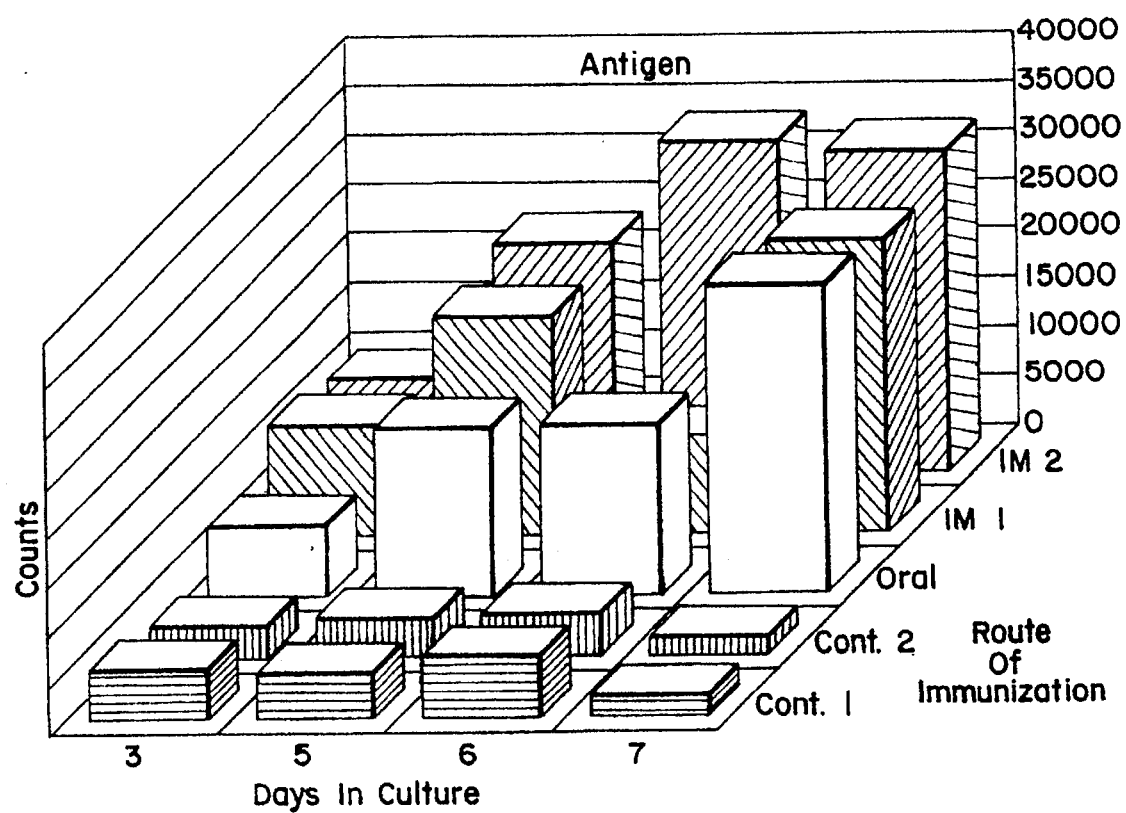
Figure 14A:
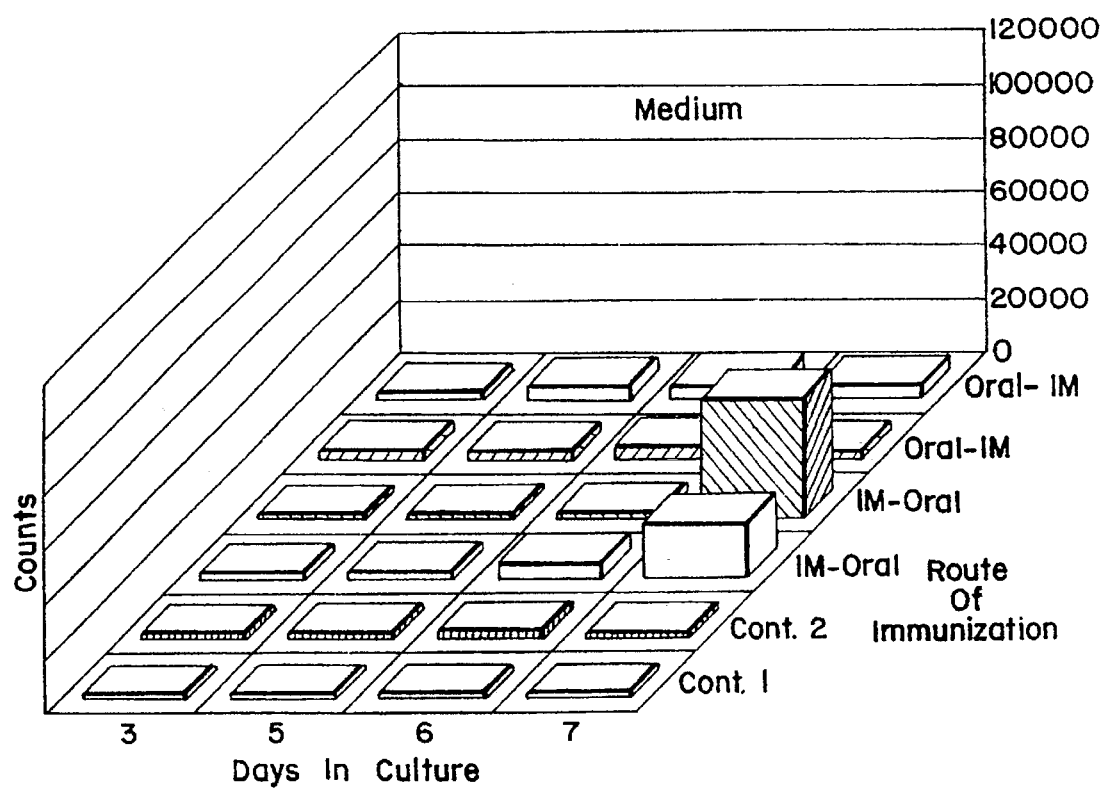
Figure 14B:
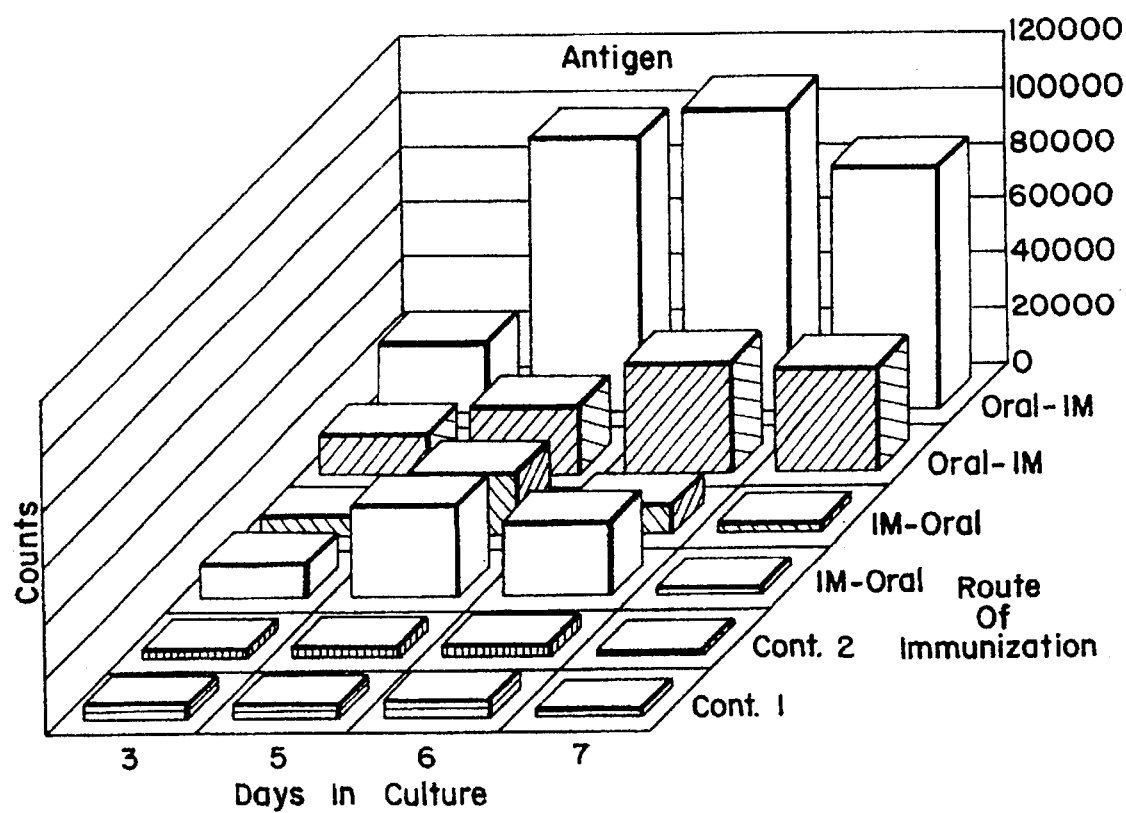
Figure 15A:
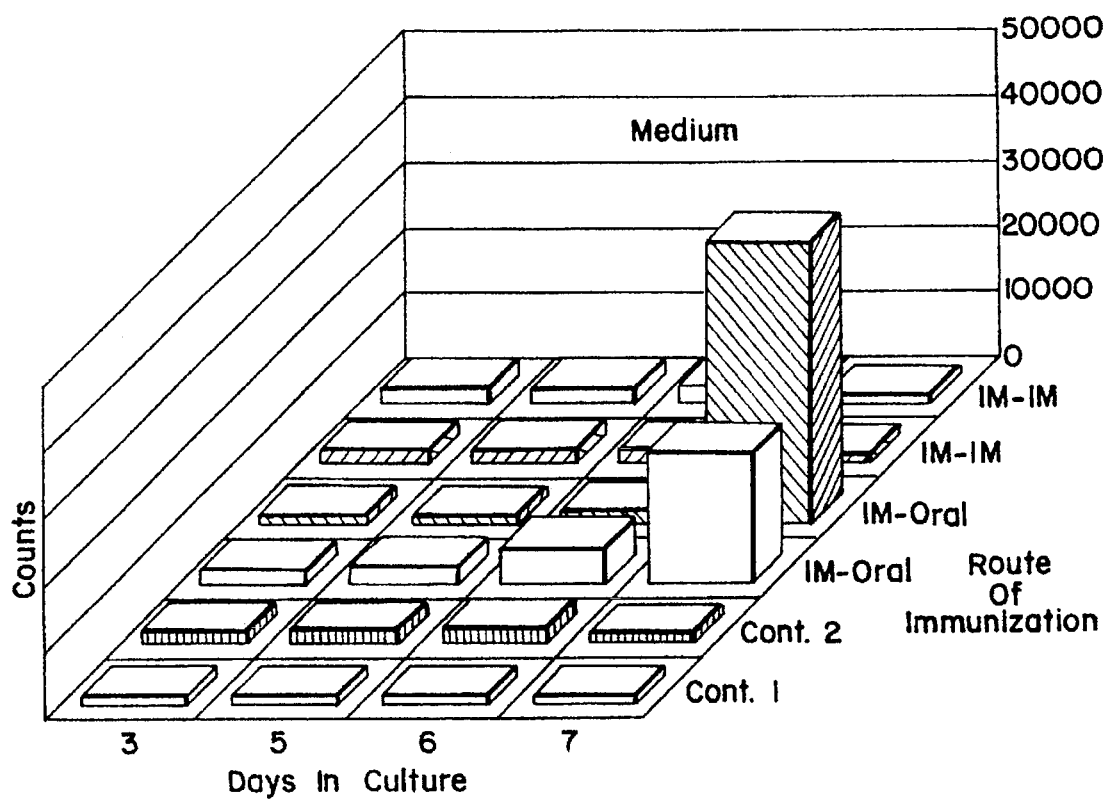
Figure 15B:
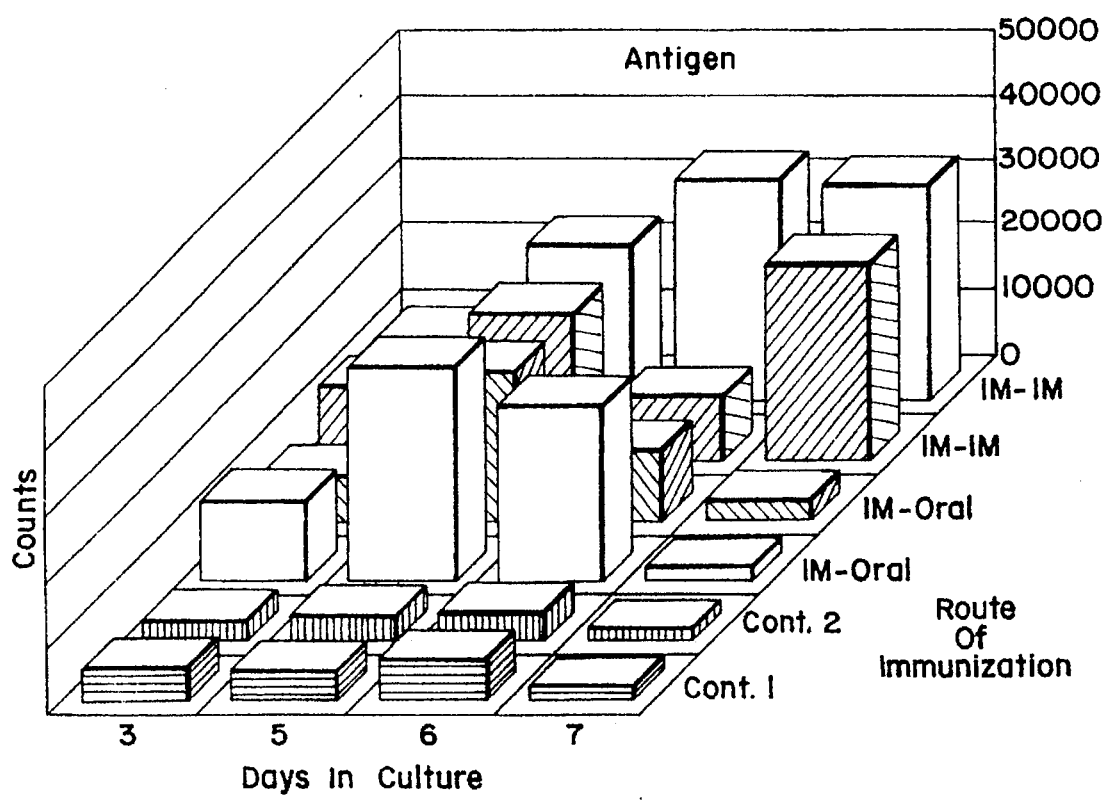
Figure 16A:
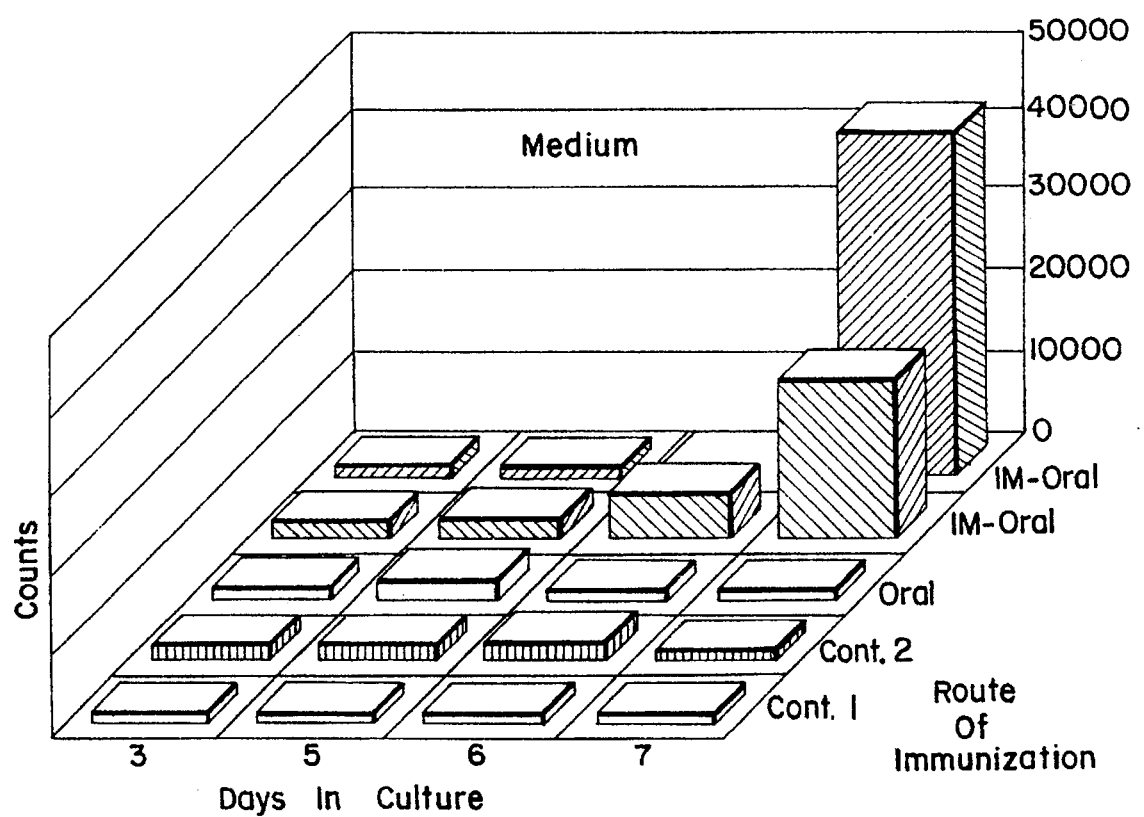
Figure 16B:
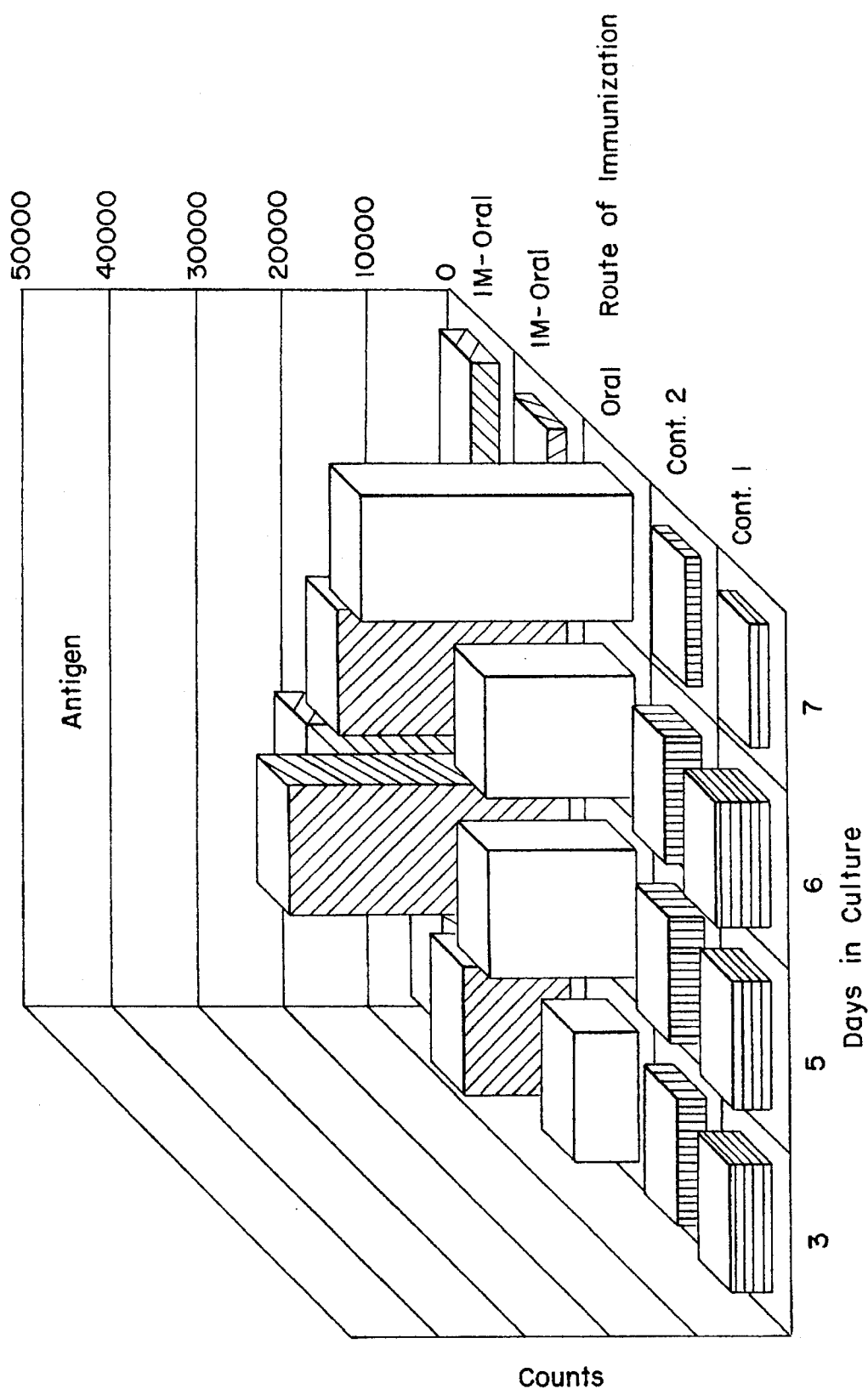

Balb C mice were immunized three times by a variety of protocols with cochleates containing 50 µg influenza glycoprotein at 0 and 3 weeks and with 12.5 µg at 14 weeks. Some mice were sacrificed at 15 weeks and their spleens removed. (FIGS. 12(A) and (B), 13(A) and (B), 14(A) and (B), 15(A) and (B) and 16(A) and (B)). Part (B) of each figure shows the proliferative response to ultraviolet light-irradiated influenza virus over several days in culture. Part (A) shows the response to media as a control. Proliferative responses are measured for DNA synthesis by $^3$H-Thd uptake into cells. All routes led to antigen-specific proliferation. Oral primary followed by 2 IM boosts gave the highest response, with 3 oral immunizations were a close second.

EXAMPLE 7

CYTOLYTIC ACTIVITY IS GENERATED UPON IMMUNIZATION WITH SENDAI COCHLEATES

Figure 17:
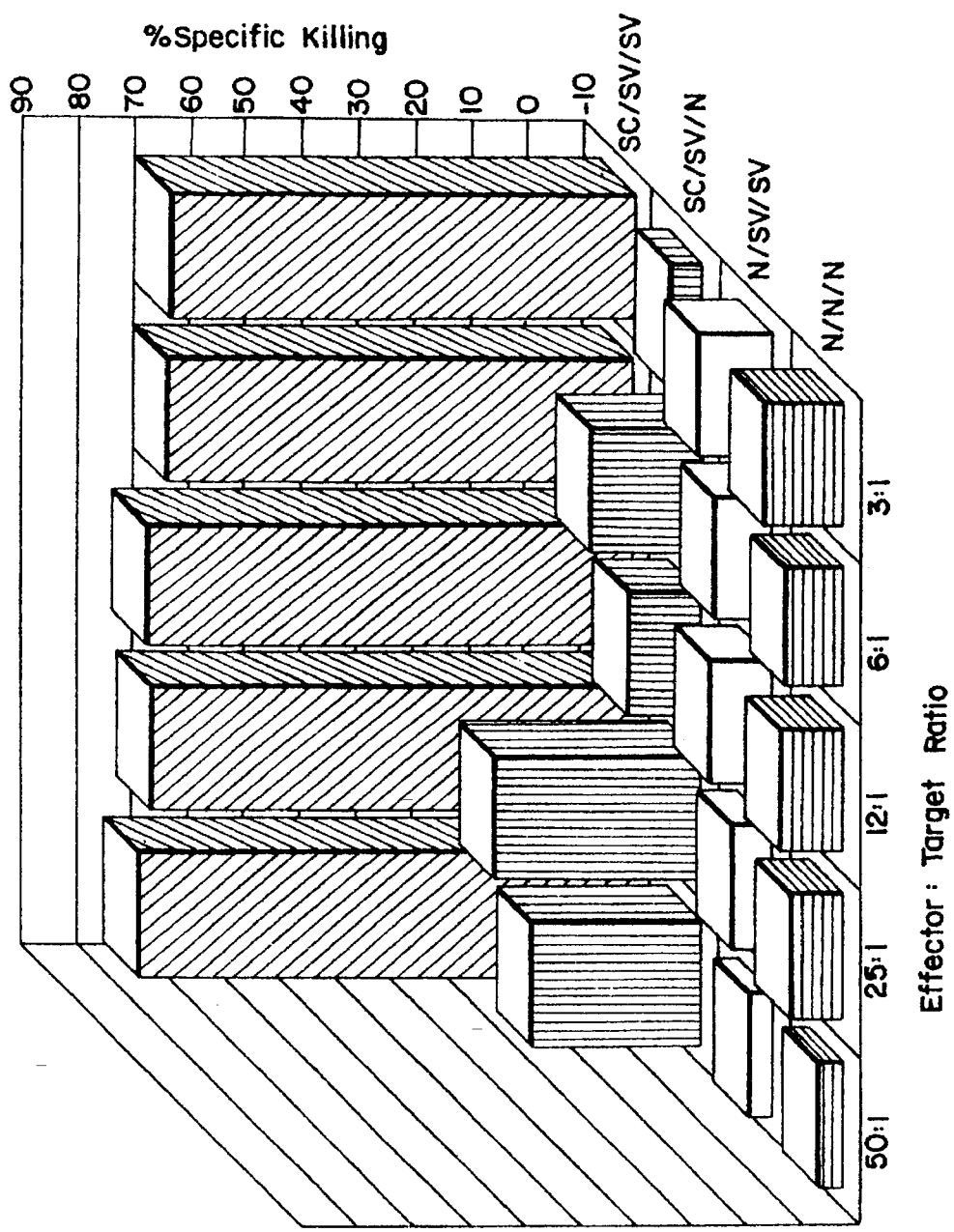
FIG. 17 is a graph depicting the induction of antigen specific cytotoxic spleenocites following oral administration of Sendai-cochleates.

A 50 µg protein dose of Sendai glycoprotein-containing cochleates was given orally. Two weeks later the animal (Balb/C mouse) was sacrificed and spleen cells obtained. Cytolytic activity of the spleen cells was measured by their ability to cause the release of Chromium 51 from target cells presenting Sendai antigens. The non-immunized mouse did not kill Sendai virus (SV) pulsed cells with in culture restimulation (N/SV/SV) or non-Sendai presenting cells (N/N/N). (FIG. 17). In contrast, Sendai cochleate immunized mice killed SV pulsed targets to a very high degree and non-pulsed targets to a lesser degree. Cytolytic activity is crucial to clearance of cells infected with viruses, or intracellular parasites or to cancer cells. It is a highly desirable activity for a vaccine to induce, but classically has not been seen with most non-living vaccines. This is an important feature of protein-cochleate vaccines.

EXAMPLE 8

PEPTIDE COCHLEATE VACCINES GIVEN ORALLY GENERATE ANTIBODY RESPONSES

Figure 18:
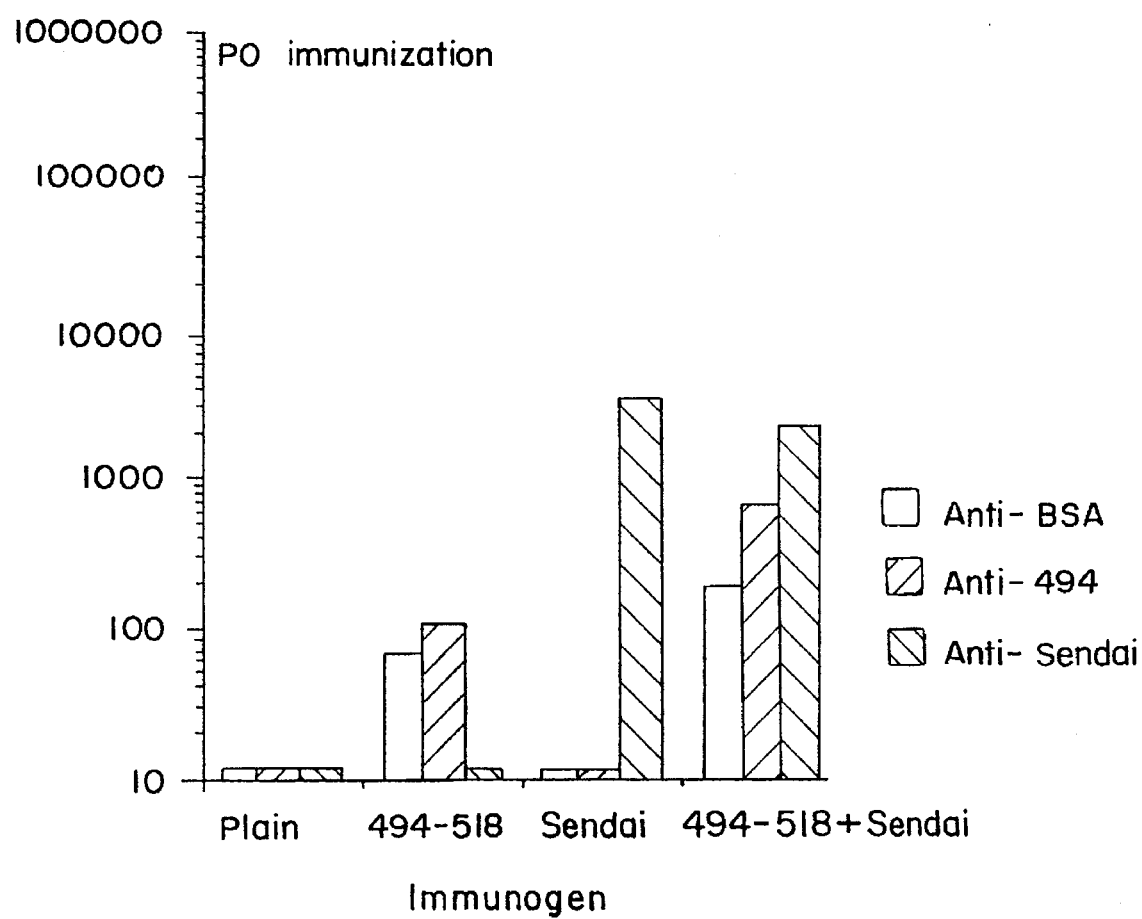
FIG. 18 shows the antibody responses following oral administration of cochleates containing Sendai glycoproteins, a peptide linked to phosphatidylethanolamine or both Sendai and PE-linked peptide.
Figure 19:
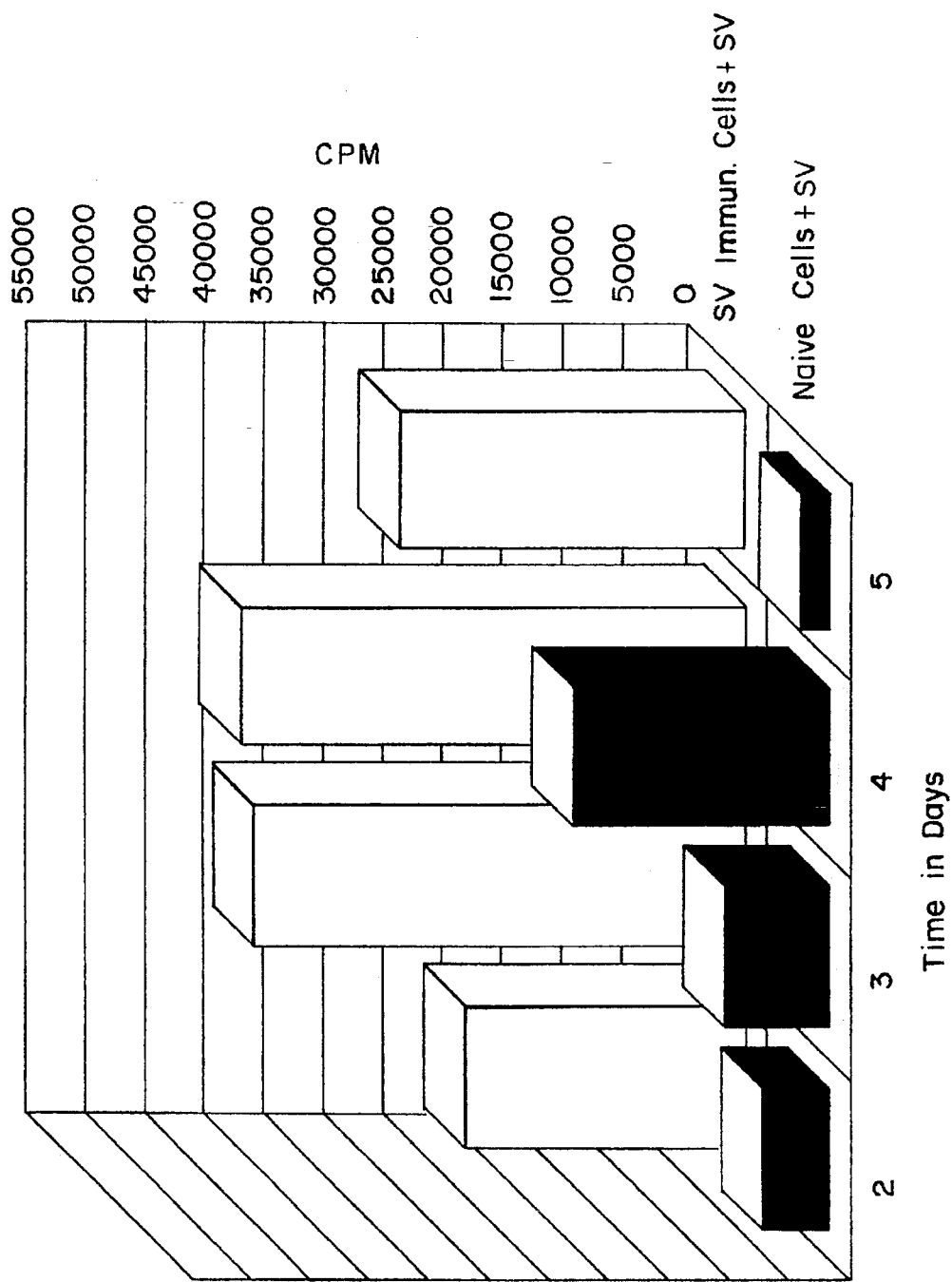
FIG. 19 is a graph showing Peyer's Patch proliferation after oral administration of Sendai-cochleates.

Cochleates containing a peptide from the surface glycoprotein of the AIDS virus cross-linked to phosphatidylethanolimine were given to mice orally three times (0, 3 and 6 weeks). (FIG. 18). In addition, cochleates containing only Sendai glycoproteins or Sendai plus the HIV peptide (amino acids 494–518) were given to separate groups of mice. Serum antibody levels were determined by ELISA. When 494–518 was formulated alone, significant antibody titers were not seen. However, with Sendai a titer of 1000 was obtained to the peptide and 2000 to Sendai. The ability to stimulate circulating antibody responses to a peptide given orally represents a significant achievement for this new class of vaccines.

EXAMPLE 9

ORAL IMMUNIZATION WITH SENDAI-COCHLEATES STIMULATES MUCOSAL CELL MEDIATED RESPONSES

Balb C mice were given cochleates containing 50 µg of Sendai glycoproteins orally and intraperitoneally simultaneously. They were sacrificed 2 weeks later, and Peyer's Patches were obtained by cutting from the surface of the small intestine. Cells isolated from the Peyer's Patches were incubated in culture with ultraviolet light-inactivated Sendai virus as a stimulatory antigen. Proliferation was measured as $^3$H-Thd uptake. It can be seen that while cells from a naive (unimmunized) mouse proliferate to some degree in response to Sendai virus, the immunized animal proliferated to a much greater degree. This indicates that the Sendai cochleares survived the stomach to be taken up by the microfold (M) cells of the small intestine and stimulated the T helper cells present there. The ability to do this is crucial to a successful oral vaccine.

While the invention has been described in detail and with reference to specific embodiments thereof, it will be apparent to one skilled in the art that various changes and modifications can be made therein without departing from the spirit and scope thereof.

What is claimed is:

1. A method of immunizing a host, comprising administering a biologically effective amount of a protein- or peptide-cochleate which comprises the following components:
   a) a protein or peptide component to which an immune response is elicited,
   b) a negatively charged lipid component, and
   c) a divalent cation component.

2. The method of claim 1, wherein the component a) is a peptide.

3. The method of claim 2, wherein the peptide is hydrophobic.

4. The method of claim 2, wherein the peptide is covalently linked to a phospholipid.

5. The method of claim 1, wherein the component a) is glycoprotein.

6. The method of claim 1, wherein the component a) is membrane protein.

7. The method of claim 1, wherein the component a) is membrane glycoprotein.

8. The method of claim 1, wherein the protein or peptide component is from a bacterial or animal virus.

9. The method of claim 8, wherein the protein component is membrane glycoprotein from Sendai virus.

10. The method of claim 8, wherein the protein component is membrane glycoprotein from influenza virus.

11. The method of claim 1, wherein the protein or peptide component is from a bacterium.

12. The method of claim 1, wherein the protein or peptide component is from a parasite.

13. The method of claim 1, wherein the protein or peptide component is from an animal cell.

14. The method of claim 13, wherein the animal cell is from a mammal.

15. The method of claim 14, wherein the mammal is a human being.

16. The method of claim 1, wherein the protein or peptide component is from an animal tissue.

17. The method of claim 16, wherein the animal tissue is from a mammal.

18. The method of claim 17, wherein the mammal is a human being.

19. The method of claim 1, wherein the negatively charged lipid component is phospholipid.

20. The method of claim 1, wherein the phospholipid is selected from the group consisting of phosphatidylserine, phosphatidylglycerol, phosphatidylinositol, and phosphatidic acid.

21. The method of claim 1, wherein the divalent cation component is a cationic compound capable of chelating and complexing negatively charged lipids.

22. The method of claim 21, wherein the divalent cation component is selected from the group consisting of $Ca^{++}$, $Mg^{++}$, $Ba^{++}$ and $Zn^{++}$.

23. The method of claim 22, wherein the divalent cation component is $Ca^{++}$.

24. The method of claim 1, wherein said administering is by a peroral route.

25. The method of claim 1, wherein said administering is by an intramuscular, a subcutaneous, an intradermal, an intranasal, an intra-ocular, an intraperitoneal, an intravaginal, an intra-rectal or a lung aerosol route.

26. The method of claim 22, wherein the divalent cation component is $Ca^{++}$ or $Mg^{++}$.

* * * * *